US010220110B2

(12) United States Patent
Kim et al.

(10) Patent No.: US 10,220,110 B2
(45) Date of Patent: Mar. 5, 2019

(54) ULTRAVIOLET STERILIZATION LAMP, ULTRAVIOLET STERILIZATION MODULE, AND AIR CONDITIONER INCLUDING ULTRAVIOLET STERILIZATION MODULE

(71) Applicant: LG ELECTRONICS INC., Seoul (KR)

(72) Inventors: Taeyoung Kim, Seoul (KR); Jaeyoul Joung, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 149 days.

(21) Appl. No.: 15/363,036

(22) Filed: Nov. 29, 2016

(65) Prior Publication Data

US 2018/0021469 A1    Jan. 25, 2018

(30) Foreign Application Priority Data

Jul. 22, 2016    (KR) .................. 10-2016-0093706

(51) Int. Cl.
    *A61L 9/20*        (2006.01)
    *F24F 13/20*      (2006.01)
    (Continued)

(52) U.S. Cl.
    CPC .............. *A61L 9/20* (2013.01); *F24F 1/0007* (2013.01); *F24F 1/0025* (2013.01); *F24F 3/16* (2013.01);
    (Continued)

(58) Field of Classification Search
    CPC ...... F24F 2003/1667; F24F 2003/1664; A61L 9/20; A61L 2209/16; A61L 2/10;
    (Continued)

(56) References Cited

U.S. PATENT DOCUMENTS 5,043,634 A     8/1991   Rothwell, Jr. et al.
5,353,085 A *   10/1994   Kurematsu ............ G03D 3/065
                                                                                                              204/528

(Continued)

FOREIGN PATENT DOCUMENTS

KR    10-2003-0091688      12/2003
KR    10-2005-0083416       8/2005

(Continued)

OTHER PUBLICATIONS

United States Office Action dated Sep. 7, 2017 issued in U.S. Appl. No. 15/368,920.

(Continued)

*Primary Examiner* — David A Vanore
(74) *Attorney, Agent, or Firm* — Ked & Associates LLP

(57) ABSTRACT

A ultraviolet (UV) sterilization lamp, a UV sterilization module, and an air conditioner including a UV sterilization module are provided. The UV sterilization module may include a porous frame, a portion of which may be a mesh so as to allow a fluid to pass therethrough; a plurality of UV lamps provided on the mesh of the porous frame and including an external electrode on an outer surface thereof; a power supply connected to the plurality of UV lamps to supply power to the plurality of UV lamps; and a plurality of fixing portions configured to support the plurality of UV lamps and fixed to the porous frame. The plurality of fixing portions may be arranged to be spaced from each other such that the plurality of UV lamps may be arranged with a constant spacing. The constant spacing may be a shortest distance of about 8 cm or less to connect outer peripheral surfaces of the plurality of UV lamps adjacent to each other.

17 Claims, 18 Drawing Sheets

(51) Int. Cl.
*F24F 1/0007* (2019.01)
*F24F 1/0025* (2019.01)
*F24F 13/22* (2006.01)
*F24F 13/28* (2006.01)
*F24F 13/30* (2006.01)
*F24F 3/16* (2006.01)
*F24F 1/00* (2019.01)

(52) U.S. Cl.
CPC .......... *F24F 13/20* (2013.01); *F24F 13/222* (2013.01); *F24F 13/28* (2013.01); *F24F 13/30* (2013.01); *A61L 2209/15* (2013.01); *F24F 2001/0048* (2013.01); *F24F 2003/1667* (2013.01)

(58) Field of Classification Search
CPC .......... B03C 3/155; B03C 3/49; B01J 19/123; B01J 2219/0875; Y02A 50/22; C02F 1/30; C02F 1/32
USPC ..... 422/121, 186.3, 24, 305, 307, 5; 96/224, 96/16, 80, 15; 210/502.1, 510.1; 250/454.11, 455.11; 454/237
See application file for complete search history.

(56) References Cited

U.S. PATENT DOCUMENTS

| | | | |
|---|---|---|---|
| 5,558,158 A | 9/1996 | Elmore | |
| 5,879,435 A * | 3/1999 | Satyapal | F24F 3/166 96/16 |
| 5,993,749 A | 11/1999 | Adams | |
| 6,685,890 B1 | 2/2004 | Van Remmen | |
| 7,773,081 B2 | 8/2010 | Olson | |
| 7,852,005 B2 | 12/2010 | Misono et al. | |
| 8,018,130 B2 | 9/2011 | Van Den Broek et al. | |
| 8,124,012 B2 | 2/2012 | Leroux et al. | |
| 8,232,715 B2 | 7/2012 | Kusunoki et al. | |
| 8,269,420 B2 | 9/2012 | Morizawa et al. | |
| 8,304,974 B2 | 11/2012 | Watanabe et al. | |
| 8,475,725 B1 | 7/2013 | Antipenko et al. | |
| 9,182,135 B2 * | 11/2015 | Rothfuss | F24F 13/18 |
| 9,518,487 B2 * | 12/2016 | Coelho Ferreira | F01N 3/035 |
| 9,873,128 B2 * | 1/2018 | Kim | B03C 3/47 |
| 9,895,462 B2 * | 2/2018 | Law | A61L 9/00 |
| 9,963,017 B2 * | 5/2018 | Kim | B60H 3/00 |
| 9,974,881 B2 * | 5/2018 | Kim | A61L 9/205 |
| 2001/0023593 A1 * | 9/2001 | Sato | F24F 1/0007 62/176.1 |
| 2001/0025570 A1 * | 10/2001 | Fukushima | B03C 3/12 95/57 |
| 2003/0042197 A1 * | 3/2003 | Kondou | B01D 39/2055 210/502.1 |
| 2003/0099569 A1 * | 5/2003 | Lentz | A61L 9/20 422/24 |
| 2003/0180200 A1 * | 9/2003 | Reisfeld | A61L 9/205 422/186.3 |
| 2003/0217561 A1 | 11/2003 | Shindo et al. | |
| 2003/0230477 A1 | 12/2003 | Fink et al. | |
| 2004/0007000 A1 * | 1/2004 | Takeda | A61L 9/22 62/78 |
| 2004/0018125 A1 * | 1/2004 | Yang | A61L 9/205 422/186.3 |
| 2004/0140269 A1 | 7/2004 | Chang | |
| 2004/0200228 A1 * | 10/2004 | Yanagimachi | B60H 1/00742 62/180 |
| 2004/0226813 A1 * | 11/2004 | Wang | B01D 53/86 204/157.3 |
| 2004/0232846 A1 | 11/2004 | Fischer et al. | |
| 2004/0251810 A1 | 12/2004 | Hsu | |
| 2005/0186124 A1 | 8/2005 | Fink et al. | |
| 2005/0204713 A1 * | 9/2005 | Wu | B01D 46/0005 55/496 |
| 2005/0238551 A1 * | 10/2005 | Snyder | A61L 9/205 422/186.3 |
| 2006/0000360 A1 * | 1/2006 | Shou | A61L 9/20 96/224 |
| 2006/0016336 A1 * | 1/2006 | Taylor | B03C 3/08 96/25 |
| 2006/0016337 A1 * | 1/2006 | Taylor | B03C 3/08 96/25 |
| 2006/0018808 A1 * | 1/2006 | Taylor | B01D 53/32 422/186.04 |
| 2006/0018810 A1 * | 1/2006 | Taylor | B01D 53/32 422/186.04 |
| 2006/0021375 A1 * | 2/2006 | Wetzel | F24F 1/025 62/419 |
| 2006/0096459 A1 | 5/2006 | Iwano et al. | |
| 2006/0113885 A1 | 6/2006 | Iimura | |
| 2006/0263275 A1 | 11/2006 | Lobach | |
| 2006/0278075 A1 * | 12/2006 | Blackner | B03C 3/016 95/57 |
| 2007/0020159 A1 * | 1/2007 | Tsui | A61L 9/22 422/186.04 |
| 2008/0030654 A1 | 2/2008 | Slutsky et al. | |
| 2008/0073565 A1 * | 3/2008 | Jeon | A61L 9/205 250/455.11 |
| 2008/0092742 A1 | 4/2008 | Marra | |
| 2008/0112845 A1 * | 5/2008 | Dunn | A61L 9/205 422/24 |
| 2008/0274018 A1 * | 11/2008 | Kawai | A01M 29/12 422/122 |
| 2008/0286163 A1 | 11/2008 | Garfield et al. | |
| 2009/0010801 A1 * | 1/2009 | Murphy | B01D 46/0028 422/4 |
| 2009/0168433 A1 | 7/2009 | Frick | |
| 2009/0202397 A1 * | 8/2009 | Parker | B01D 53/8675 422/121 |
| 2010/0047115 A1 * | 2/2010 | Krichtafovitch | A61L 9/16 422/4 |
| 2010/0106787 A1 * | 4/2010 | Grohman | G05B 15/02 709/206 |
| 2010/0134000 A1 | 6/2010 | Carter et al. | |
| 2010/0150793 A1 * | 6/2010 | Chan | A61L 2/10 422/186.3 |
| 2011/0227501 A1 | 9/2011 | Awamoto et al. | |
| 2012/0085927 A1 * | 4/2012 | Maeng | A61L 9/20 250/454.11 |
| 2012/0153804 A1 | 6/2012 | Li | |
| 2012/0171945 A1 * | 7/2012 | Lee | A01M 1/023 454/237 |
| 2012/0199005 A1 | 8/2012 | Koji et al. | |
| 2012/0319011 A1 | 12/2012 | Brabham et al. | |
| 2013/0192288 A1 | 8/2013 | Willette | |
| 2014/0157989 A1 | 6/2014 | Kirschman | |
| 2014/0178254 A1 * | 6/2014 | Tsui | A61L 9/22 422/121 |
| 2015/0228470 A1 | 8/2015 | Ruiz | |
| 2015/0262780 A1 | 9/2015 | Eaton | |
| 2016/0243559 A1 * | 8/2016 | Kim | B03C 3/47 |
| 2018/0021468 A1 * | 1/2018 | Kim | A61L 9/20 |
| 2018/0021469 A1 * | 1/2018 | Kim | A61L 9/20 |
| 2018/0021470 A1 * | 1/2018 | Kim | A61L 9/20 |
| 2018/0023820 A1 * | 1/2018 | Kim | F24F 1/0007 |
| 2018/0023821 A1 * | 1/2018 | Kim | A61L 9/20 62/264 |
| 2018/0104374 A1 * | 4/2018 | Kim | A61L 9/205 |

FOREIGN PATENT DOCUMENTS

| | | |
|---|---|---|
| KR | 10-2006-0035144 | 4/2006 |
| KR | 10-2006-0039360 | 5/2006 |
| KR | 10-0725763 | 5/2007 |

OTHER PUBLICATIONS

U.S. Office Action issued in U.S. Appl. No. 15/299,622 dated Mar. 26, 2018.

(56) References Cited

OTHER PUBLICATIONS

U.S. Office Action dated Aug. 3, 2017 issued in U.S. Appl. No. 15/363,071.

* cited by examiner

ULTRAVIOLET STERILIZATION LAMP, ULTRAVIOLET STERILIZATION MODULE, AND AIR CONDITIONER INCLUDING ULTRAVIOLET STERILIZATION MODULE

CROSS-REFERENCE TO RELATED APPLICATION(S)

The present application claims priority under 35 U.S.C. 119 and 35 U.S.C. 365 to Korean Patent Application No. 10-2016-0093706, filed in Korea on Jul. 22, 2016, which is hereby incorporated by reference in its entirety.

BACKGROUND

1. Field

An ultraviolet (UV) sterilization lamp, an UV sterilization module, and an air conditioner including a UV sterilization module are disclosed herein.

2. Background

Generally, a UV lamp is used in various fields so as to sterilize bacteria and fungus by generating UV rays. As the UV lamp is in the form of a lamp, the UV lamp may be appropriately used with simple manipulation when necessary. Further, installation costs and maintenance costs of the UV lamp are inexpensive. Moreover, as UV rays generated by the UV lamp are hardly changed, the UV rays continuously maintain a same sterilizing power.

The UV lamp generates UV rays having various wavelengths according to a material used therein. For example, the UV lamp may generate UV-A (wavelength of 400 nm to 315 nm), UV-B (wavelength of 15 nm to 280 nm), or UV-C (wavelength of 280 nm to 110 nm), for example. Among these wavelength, the UV rays having a wavelength of 253.7 nm at a wavelength corresponding to the UV-C have a strongest sterilizing power. When the UV-C is irradiated to a DNA of the bacteria and fungus, the DNA of the bacteria and fungus is damaged and destroyed. That is, the UV rays damage a DNA of a living organism and has an effective sterilizing power with respect to various bacteria.

Therefore, sterilization using the UV lamp is more efficient than sterilization by heat, sterilization by chemicals, sterilization by ozone, and sterilization by radiation, for example. However, as the UV rays damage the DNA of the living organism, great care is needed not to irradiate the UV rays to people, for example.

On the other hand, the sterilization is effective only when the UV lamp receives power and generates the UV rays. Thus, an important issue is to improve a lifespan of the UV sterilization lamp.

Further, in order to exhibit a sterilizing power to sterilize various bacteria, the UV rays generated by the UV sterilization lamp needs to be uniformly irradiated for a predetermined period of time. Thus, another important issue is to irradiate uniform UV rays on a uniform plane.

For example, as disclosed in Korean Patent Application Publication No. 10-2003-0091688, which is entitled "AIR CONDITIONER" and hereby incorporated by reference, a UV lamp may be installed in an air conditioner. However, the prior art UV lamp is large in size, and thus, has a shortcoming in terms of space efficiency and air channel.

Further, even when a large-sized UV lamp is installed, a uniform plane may not be uniformly sterilized. Moreover, the large-sized UV lamp has high power consumption. When a large number of UV lamps is used, electric charges may be increased due to an increase in power facility expansion costs and power consumption for satisfying power to be consumed.

BRIEF DESCRIPTION OF THE DRAWINGS

Embodiments will be described in detail with reference to the following drawings in which like reference numerals refer to like elements, and wherein.

DETAILED DESCRIPTION

Figure 1:
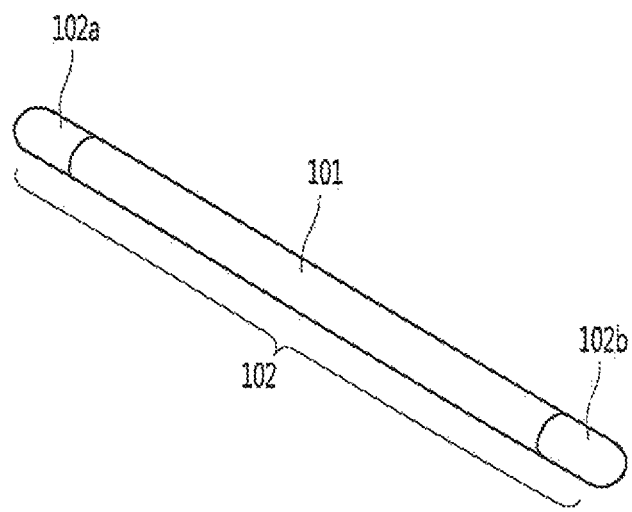
FIG. 1 is a perspective view of a UV sterilization lamp according to an embodiment.

Examples of various embodiments are illustrated in the accompanying drawings and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

Example embodiments will be described in more detail with reference to the accompanying drawings. The embodiments, however, may be embodied in various different forms, and should not be construed as being limited to only the illustrated embodiments herein. Rather, these embodiments are provided as examples so that this disclosure will be thorough and complete, and will fully convey the aspects and features to those skilled in the art.

It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, s, operations, elements, and/or components, but do not preclude the presence or addition of one or more other features, integers, s, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

Spatially relative terms, such as "beneath," "below," "lower," "under," "above," "upper," and the like, may be used herein for ease of explanation to describe one element or feature's relationship to another element s or feature s as illustrated in the figures. It will be understood that the spatially relative terms are intended to encompass different orientations of the device in use or in operation, in addition to the orientation depicted in the figures. For example, if the device in the figures is turned over, elements described as "below" or "beneath" or "under" other elements or features would then be oriented "above" the other elements or features. Thus, the example terms "below" and "under" can encompass both an orientation of above and below. The device may be otherwise oriented for example, rotated 90 degrees or at other orientations, and the spatially relative descriptors used herein should be interpreted accordingly.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the following description, numerous specific details are set forth in order to provide a thorough understanding of the present disclosure. The embodiments may be practiced without some or all of these specific details. In other instances, well-known process structures and/or processes have not been described in detail in order not to unnecessarily obscure the present disclosure.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

Hereinafter, embodiments will be described in details with reference to attached drawings.

Figure 2:
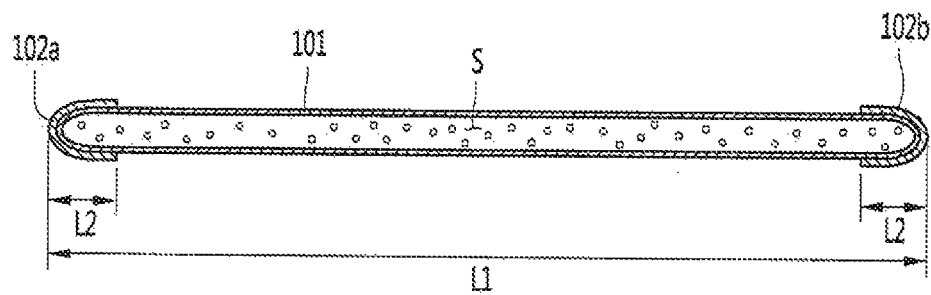
FIG. 2 is a vertical cross-sectional view of the UV sterilization lamp of FIG. 1.
Figure 3:
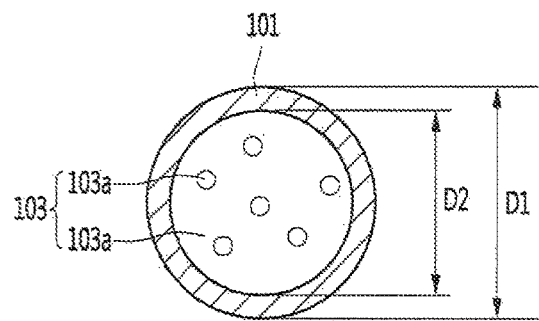
FIG. 3 is a horizontal cross-sectional view of the UV sterilization lamp of FIG. 1.

FIG. 1 is a perspective view of a UV sterilization lamp according to an embodiment. FIG. 2 is a vertical cross-sectional view of the UV sterilization lamp of FIG. 1. FIG. 3 is a horizontal cross-sectional view of the UV sterilization lamp of FIG. 1.

Referring to FIGS. 1 and 3, the UV sterilization lamp 100 according to this embodiment may include a lamp body 101 forming an outer appearance and having an internal space S. The lamp body 101 may have a bar, tube, or pipe shape, for example, to define the internal space S. A cut cross-section of the lamp body 101 may have various shapes, such as a circular shape, a polygonal shape, or an oval shape, for example. A hollow may be formed inside of the cut cross-section. The hollow may be formed to have various shapes, such as a circular shape, a polygonal shape, or an oval shape, for example. However, embodiments are not limited thereto, and UV rays generated by the UV sterilization lamp 100 may be formed to have a circular shape so that the UV rays are uniformly irradiated in all directions. When the lamp body 101 has a circular shape, the lamp body 101 may have a constant outer diameter D1 and a constant inner diameter D2. Desirable dimensions of the outer diameter D1 and the inner diameter D2 of the lamp body 101 will be described in detail below with reference to FIGS. 5A-5C.

The lamp body 101 may be provided to be elongated in a lengthwise direction. A length L1 of the lamp body 101 may be variously provided according to an apparatus on which the UV sterilization lamp 100 is mounted. For example, when the UV sterilization lamp 100 is provided in a wall-mounted air conditioner, the lamp body may have a length of at least about 60 cm to about 70 cm. Further, when the UV sterilization lamp 100 is provided in an air cleaner, the lamp body may have a length of at least about 20 cm to about 50 cm. However, embodiments are not limited thereto, and the lamp body may have various lengths. Therefore, in this embodiment, the lamp body 101 may be formed to have a circular shape and may be formed to have a long straight pipe shape.

The lamp body 101 may be made of a material through which the UV rays generated in the internal space S may be easily transmitted to the outside. For example, the lamp body 101 may be made of quartz, borosilicate, or a glass containing the quartz or the borosilicate, for example. As the quartz has excellent permeability, loss of the UV rays may be minimized.

The internal space S may be understood as a closed space provided inside of the lamp body 101. An emission material 103 that generates the UV rays may be enclosed in the internal space S. The internal space S of the lamp body may be sealed in a state in which the emission material 103 is filled. Therefore, the internal space S may form a space where no materials are introduced from the outside.

The emission material 103 may be understood as a material capable of generating a UV-C wavelength having excellent sterilizing power. The emission material 103 may be provided in a gas state and may further include a small amount of mixture. The emission material 103 may be a mixture of different emission materials 103 of a gas state.

The emission material 103 may include one or more of Hg, Ne, Xe, Kr, Ar, XeBr, XeCl, KrBr, KrCl, and $CH_4$. Further, except for Hg, all of the emission materials 103 may be present in a gas state. Thus, the materials except for Hg may be referred to as a "charging gas".

Among the emission materials 103, Ne, Xe, Kr, and Ar may be inert gases which hardly cause a chemical reaction with other elements and may be a material that generates a wavelength in a specific case. However, embodiments are not limited thereto.

Among the emission materials 103, Hg may generate UV rays having a wavelength close to a wavelength of about 253.7 nm having excellent sterilizing power. Further, a light conversion rate is most excellent with respect to power consumption applied for generating the UV rays.

On the other hand, the mercury (Hg) causes "Minamata diseases" and moves a long distance in a gas state. Thus, the mercury is designated as a harmful material which affects body health and environment. In this regard, an international convention was conducted in United Nations Emergency Forces (UNEF) so as to minimize the use of mercury. As a result, the "Minamata Convention on Mercury" was officially signed. According to the standard of the UNEF, the mercury can be contained in a range of 5 mg to 40 mg.

Further, in Korea, various standards have been proposed for a size, purpose, and manufacturing technology of lamps so as to reduce the use of mercury. As the mercury content standard in Korea, Eco-labeling certification standard (Korea Environmental Industry & Technology Institute), and LOHAS (Korean Standards Association), for example, are used. According to the Eco-labeling certification standard, 5 mg of mercury can be contained.

Therefore, in this embodiment, about 5 mg or less of mercury, which is the mercury content standard of the Minamata Convention and Korea, is used while providing UV rays close to a wavelength of about 253.7 nm. For example, the emission material 103 may be an inert gas 103b as a major part and an alloy containing a small amount of mercury. The alloy may be an amalgam 103a. The amalgam 103a may be an alloy, such as Xn+Hg, Zn+Hg, or In+Hg, for example. The amalgam 103a may be provided in a size of about 500 micrometers or more. About 95% of the inert gas 103b may be provided. Further, the inert gas 103b may be provided at a normal pressure or a medium pressure.

An external electrode unit or electrode 102 may be further included in or at an outer surface of the lamp body 101. The UV sterilization lamp 100 in accordance with this embodiment uses an external electrode scheme in which an electrode is provided on an outer surface. The external electrode scheme is a scheme that provides the external electrode unit 102 on the outer surface of the lamp body 101 and generates UV rays by discharging and exciting the emission material of the internal space S.

According to the external electrode scheme, a filament (internal electrode scheme) having been used in a conventional UV lamp is removed to thereby prevent heat generation, blackening, and lifespan reduction, for example, caused by the filament. Further, in a case of using the external electrode scheme, a lifespan may be reduced and heat generation of the lamp body 101 itself may be reduced, as compared with a UV lamp using the internal electrode scheme. Further, as the external electrode unit 102 is provided on the outer surface of the lamp body 101, a parallel connection is possible.

The external electrode unit 102 may include a first electrode unit or electrode 102a, which provides a first electrode, and a second electrode unit or electrode 102b, which provides a second electrode. The first electrode unit 102a and the second electrode unit 102b may be spaced from each other and may be provided at ends of both sides of the lamp body 101.

The external electrode unit 102 may be provided by coating a conductive liquid containing a conductive material on the outer surface of the lamp body 101. Further, the external electrode unit 102 may be provided by immersing a portion of the lamp body 101 into the conductive liquid and taking out and curing the lamp body 101.

The conductive liquid may include one or more of a bonding agent, an additive, and a solvent, for example, as well as the conductive material. The conductive material may include one or more of Ag, carbon nano-tube (CNT), Cu, or Pt, for example. The bonding agent may include an epoxy-based material, a resin-based material, or a binder, for example. Therefore, the conductive material may be easily fixed to the outer surface of the lamp body 101.

For example, the external electrode unit 102 may be a silver paste. When the silver paste is provided as the external electrode unit 102, the use of Ag is advantageous in terms of electrical conductivity, but its oxidation quickly occurs and its price is high.

Further, the external electrode unit 102 may be provided by a thin film on the outer surface of the lamp body 101 by mixing a carbon nano-tube (CNT) powder with a binder, and then, may be fixed by curing the thin film. When the external electrode unit 102 is provided as the carbon nano-tube (CNT), the price thereof is relatively low, but electrical conductivity is low as compared with Ag.

That is, there is no limitation in a method of providing the conductive liquid containing the conductive material to the outer surface of the lamp body 101.

In this embodiment, it has been assumed that the external electrode unit 102 is provided by the conductive liquid, but a cap-shaped external electrode may also be inserted onto the outer surface of the lamp body 101. However, embodiments are not limited thereto.

The external electrode unit 102 may have a length L2 of about 1 cm to about 3 cm at ends of both sides of the lamp body 101. The external electrode unit 102 may be provided in a lengthwise direction of the lamp body 101 at the ends of both sides of the lamp body 101.

When the external electrode unit 102 has a length below about 1 cm, it may be difficult to discharge and excite the emission material 103 in the lamp body 101. That is, the external electrode unit 102 may have a small area to lower discharge and excitation efficiency of the emission material 103.

When the external electrode unit 102 has a length above about 3 cm, it may not be difficult to discharge and excite the emission material 103 in the lamp body 101, but the UV emission area may be smaller due to a smaller area of the external electrode unit 102. Therefore, in this embodiment, the external electrode unit 102 may have a length L2 of about 1 cm to about 3 cm at the ends of both sides of the lamp body 101. Further, the length of the external electrode unit 102 may also increase as the outer diameter and the inner diameter of the lamp body 101 increase. That is, the length of the external electrode unit 102 may increase in proportion to the outer diameter and the inner diameter of the lamp body 101.

Figure 4:
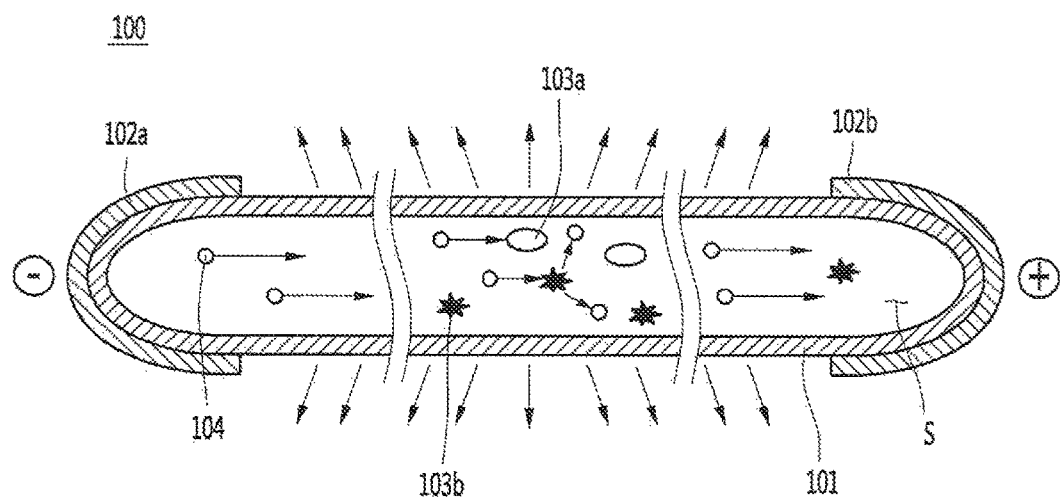
FIG. 4 is a diagram illustrating a state in which UV rays are generated by the UV sterilization lamp according to an embodiment.

FIG. 4 is a diagram illustrating a state in which UV rays are generated by the UV sterilization lamp according to an embodiment. Referring to FIG. 4, power may be supplied to the first electrode unit 102a and the second electrode unit 102b respectively arranged at the ends of both sides of the lamp body 101. For example, the first electrode unit 102a and the second electrode unit 102b may be respectively a "negative electrode" and a "positive electrode".

High-voltage power for discharging and exciting the emission material 103 in the lamp body 101 may be supplied to the first electrode unit 102a and the second electrode unit 102b. A low current may be provided as the high-voltage power. However, embodiments are not limited thereto.

When the power is supplied to the first electrode unit 102a and the second electrode unit 102b, the emission material 103 may be arranged on an electric field formed between the first electrode unit 102a and the second electrode unit 102b.

When the emission material 103 is disposed on the electric field, the emission material 103 may be discharged and excited in the closed internal space of the lamp body 101. When the emission material 103 is discharged and excited, UV rays may be generated. A wavelength of the generated UV rays may be different according to a type of the emission material 103 enclosed in the lamp body 101. In this embodiment, the emission material 103 is a material that can generate a wavelength of about 253.7 nm having the strongest sterilizing power among UV rays of the UV-C wavelength and generate wavelengths close to about 253.7 nm.

Hereinafter, the process of generating the UV rays of the UV-C wavelength by the electric field will be described with reference to FIG. 4.

The emission material 103 may be enclosed in the lamp body 101. The emission material 103 may be the inert gas 103b as a major part and an alloy containing a small amount of mercury, that is, the amalgam 103a.

Power may be supplied to the first electrode unit 102a and the second electrode unit 102b. The first electrode unit 102a and the second electrode unit 102b may be respectively the "negative electrode" and the "positive electrode". When the power is supplied, the electric field may be formed between the first electrode unit 102a and the second electrode unit 102b, and the emission material 103 may be disposed on the electric field.

When disposed on the electric field, electrons 104 present in the internal space S may move toward the second electrode unit 102b. The electrons 104 are particles having negative charges and may move toward the positive electrode (to the right in the drawing).

When the electrons 104 moves toward the second electrode unit 102b, the electrons 104 may collide with the emission material 103. Specifically, the electrons 104 may collide with the inert gas 103b and the amalgam 103a in the internal space S. At least one electron 104 may collide with the inert gas 103b enclosed in the internal space S as the major part and then increase to a plurality of electrons 104. Subsequently, the plurality of electrons 104 may continuously collide with the inert gas 103b and the amalgam 103a. The inert gas 103b, which is in a stable state, and the amalgam 103a may be ionized, discharged, and excited by the collision with the electrons 104. The mercury contained in the amalgam 103a may be discharged and excited to generate the UV rays.

Figure 5A:
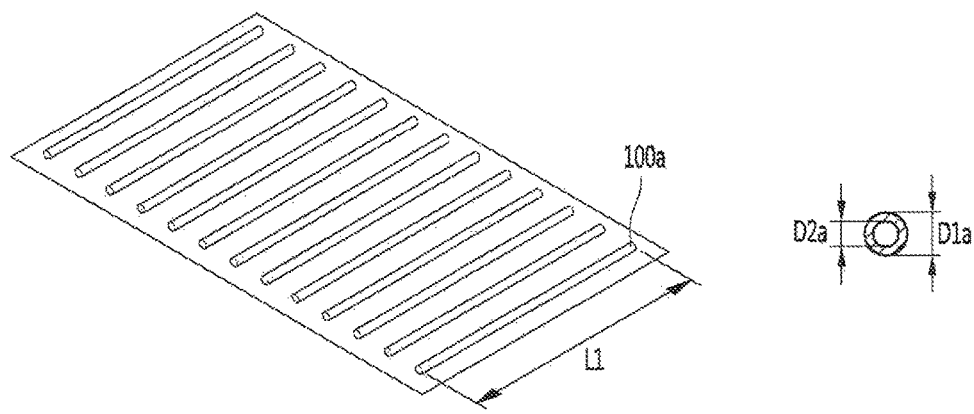
FIGS. 5A-5C are diagrams illustrating comparison of power consumption when a size of the UV sterilization lamp according to an embodiment is changed.
Figure 5B:
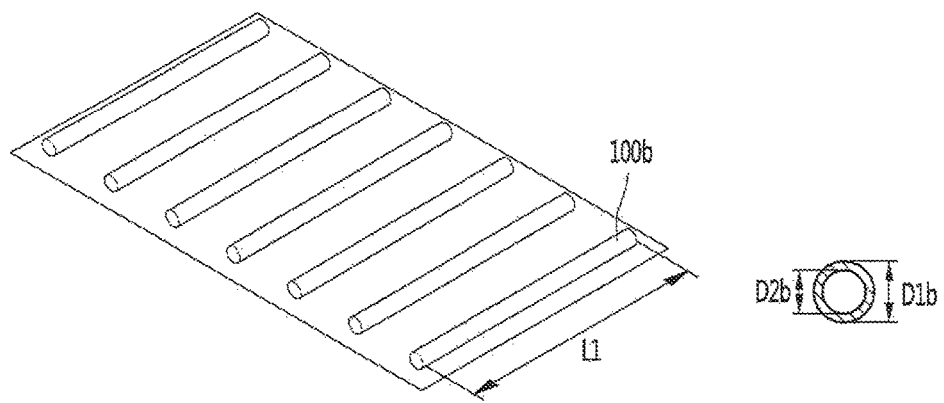
Figure 5C:
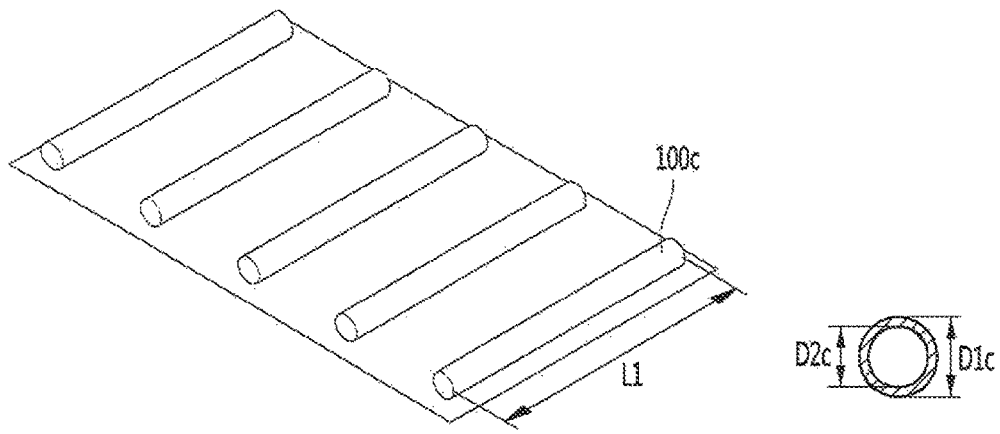

FIGS. 5A-5OC are diagrams illustrating comparison of power consumption when a size of the UV sterilization lamp according to an embodiment is changed. Referring to FIGS. 5A-5C, a plurality of UV sterilization lamps 100 may be arranged to be spaced from each other. The UV sterilization lamp 100 may be formed to have the constant outer diameter D1 (see FIG. 3) and the constant inner diameter D2 (see FIG. 3). Further, the UV sterilization lamp 100 may be formed to have the constant length L1.

An amount of the emission material 103, which may be enclosed in the UV sterilization lamp 100, may be determined by the outer diameter D1, the inner diameter D2, and the length L of the UV sterilization lamp 100. Among them, the length L1 may be changed according to a position where the UV sterilization lamp 100 is to be installed. Further, influence of the length L1 is somewhat slight as compared with the outer diameter D1 and the inner diameter D2 of the UV sterilization lamp.

Therefore, the inventors have proposed a desirable size of the UV sterilization lamp 100 according to this embodiment by fixing the length L1 of the UV sterilization lamp and changing the outer diameter D1 and the inner diameter D2 of the UV sterilization lamp.

The UV sterilization lamp 100 may affect an installation position of the UV sterilization lamp 100 in terms of hydrodynamics according to the outer diameter D1 thereof. The UV sterilization lamp 100 may be usually used to sterilize a fluid, such as water or air. Therefore, when the outer diameter D1 of the UV sterilization lamp increases, a flow of the fluid, such as water or air, in the installation position of the UV sterilization lamp 100 may be affected.

Further, an amount of the emission material 103, which may be enclosed in the internal space S of the UV sterilization lamp 100, may be determined by the inner diameter D2 of the UV sterilization lamp 100. As the amount of the emission material 103 increases or decreases, the power consumption of the UV sterilization lamp 100 may change. In other words, when the amount of the emission material 103 increases, the power consumption for discharging and exciting the emission material 103 may increase.

That is, the desirable outer diameter D1 and inner diameter D2 of the UV sterilization lamp needs to be derived by approaching in terms of hydrodynamics and power consumption.

Referring to FIG. 5A, a plurality of UV sterilization lamps 100 are arranged in parallel. The UV sterilization lamp 100 may be formed to have a first outer diameter D1a of about 1 mm, a first inner diameter D2a of about 700 micrometers, and a length L1 of about 65 cm. The UV sterilization lamp 100 having the first outer diameter D1a and the first inner diameter D2a may be referred to as a first UV sterilization lamp 100a.

The first UV sterilization lamp 100a may be formed to have a slightly small size. Thus, a slightly small amount of the emission material (103 in FIG. 4) may be enclosed in the first UV sterilization lamp 100a. The power consumption for operating the first UV sterilization lamp 100a was measured as about 0.3 to 0.5 W. Further, as the first UV sterilization lamp 100a is formed to have a slightly small size, the influence on the flow of the fluid may be slight in terms of hydrodynamics.

That is, the first UV sterilization lamp 100a may have low power consumption for operating the emission material 103. Further, as the influence on the flow of the fluid is slight, a plurality of UV sterilization lamps may be arranged adjacent to each other. Further, the first UV sterilization lamp 100a may be used in a small space.

However, as the first UV sterilization lamp 100a has a slightly small size, the first UV sterilization lamp 100a is vulnerable to external impact. Further, the first UV sterilization lamp 100a is difficult to manufacture. Further, the first inner diameter D2a of the first UV sterilization lamp has to consider the emission material 103 enclosed in the internal space S. The amalgam 103a (see FIG. 4) in the emission material 103 is a solid having a constant size, and the first inner diameter D2a has to be larger than the size of the amalgam 103a. The amalgam 103a may be provided in a size of at least about 500 micrometers. Therefore, the first inner diameter D2a needs to be formed to be at least about 700 micrometers or more such that the amalgam 103a is easily injected.

Therefore, the desirable minimum size of the first UV sterilization lamp 100a, which is proposed in this embodiment, may include the first inner diameter D2a of at least about 700 micrometers, and the first outer diameter D1a of about 1 mm or more having a thickness enough not to be damaged while including the first inner diameter D2a.

Referring to FIG. 5B, a plurality of UV sterilization lamps 100 are arranged in parallel. The UV sterilization lamp 100 may be formed to have a second outer diameter D1b of about 3 mm, a second inner diameter D2b of about 2 mm, and a length L1 of about 65 cm. The UV sterilization lamp 100 having the second outer diameter D1b and the second inner diameter D2b may be referred to as a second UV sterilization lamp 100b.

The second UV sterilization lamp 100a may be formed to be slightly larger than the first UV sterilization lamp 100a. Thus, as compared with the first UV sterilization lamp 100a, a slightly larger amount of the emission material (103 in FIG. 4) may be enclosed in the second UV sterilization lamp 100b. As a result of measurement through experiments by the inventors, the power consumption for operating the second UV sterilization lamp 100b was measured as about 2 to 3 W.

That is, as the second UV sterilization lamp 100b is larger than the first UV sterilization lamp 100a, the filled amount of the emission material 103 increases. The power consumption for discharging the emission material 103 was increased, and the power energy of the generated UV rays was increased. As the size of the second UV sterilization lamp 100b was increased, the influence on the flow of the fluid was increased. However, the increased size reduced the risk of damage.

Referring to FIG. 5C, a plurality of UV sterilization lamps 100 are arranged in parallel. The UV sterilization lamp 100 may be formed to have a third outer diameter D1c of about 7 mm, a third inner diameter D2c of about 5 mm, and a length L1 of about 65 cm. The UV sterilization lamp 100 having the third outer diameter D1c and the third inner diameter D2c may be referred to as a third UV sterilization lamp 100c.

The third UV sterilization lamp 100c may be formed to be larger than the second UV sterilization lamp 100b. Thus, as compared with the second UV sterilization lamp 100b, a larger amount of the emission material (103 in FIG. 4) may be enclosed in the third UV sterilization lamp 100c. As a result of measurement through experiments by the inventors, the power consumption for operating the third UV sterilization lamp 100c was measured as about 8 to 10 W.

That is, as the third UV sterilization lamp 100c is larger than the second UV sterilization lamp 100b, the power consumption for generating the UV rays was further increased. Further, due to the further increased power consumption, the power energy of the UV rays was further increased.

However, as the third UV sterilization lamp 100c has high power consumption for discharging the emission material 103, the generated heat may be increased. Further, the increased size may increase the influence on the flow of the fluid. Thus, the third UV sterilization lamp 100c may have high resistance to the fluid. Further, it is difficult to arrange a plurality of UV sterilization lamps to be adjacent to each other. Therefore, the desirable maximum size of the third UV sterilization lamp 100c, which is proposed in this embodiment, may include the third outer diameter D1c of about 7 mm or less.

The inner diameter D2 of the UV sterilization lamp may have a correlation proportional to the enclosed amount of the emission material 103 and the power consumption. The enclosed amount of the emission material 103 may be affected by the inner diameter D2 and the length L1 of the UV sterilization lamp 100.

The outer diameter D1 of the UV sterilization lamp may have a correlation proportional to a durability of the UV sterilization lamp and a flow resistance of the fluid in terms of hydrodynamics. Further, as a flow velocity and flow rate, for example, of the fluid is changed by the flow resistance, uniform sterilization may become difficult. Further, when the outer diameter D1 of the UV sterilization lamp increases and the generated power energy increases, the UV rays are intensively irradiated on a specific region, thus degrading a material of the specific region. Further, a region where the UV rays are not intensively irradiated may not be sterilized.

As a result, the desirable inner diameter D2 of the UV sterilization lamp 100 may be about 700 micrometers or more. The outer diameter D1 of the UV sterilization lamp 100 may be about 1 mm to about 7 mm.

Figure 6A:
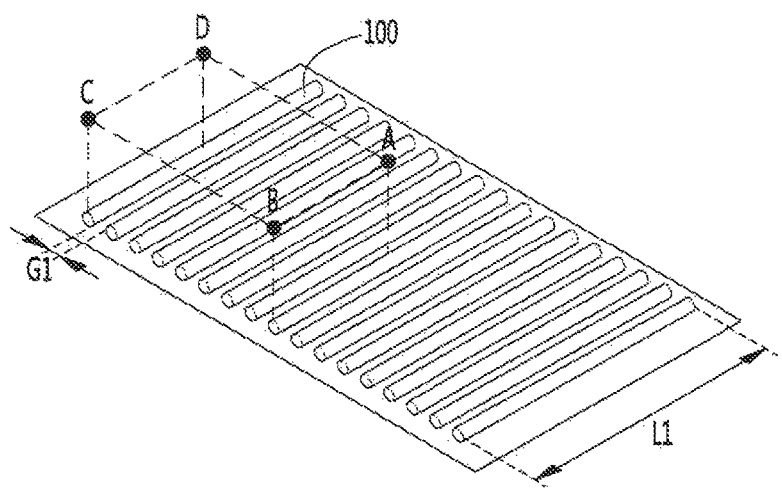
FIGS. 6A-6C are diagrams illustrating power energies measured by changing a spacing between UV sterilization lamps according to an embodiment.
Figure 6B:
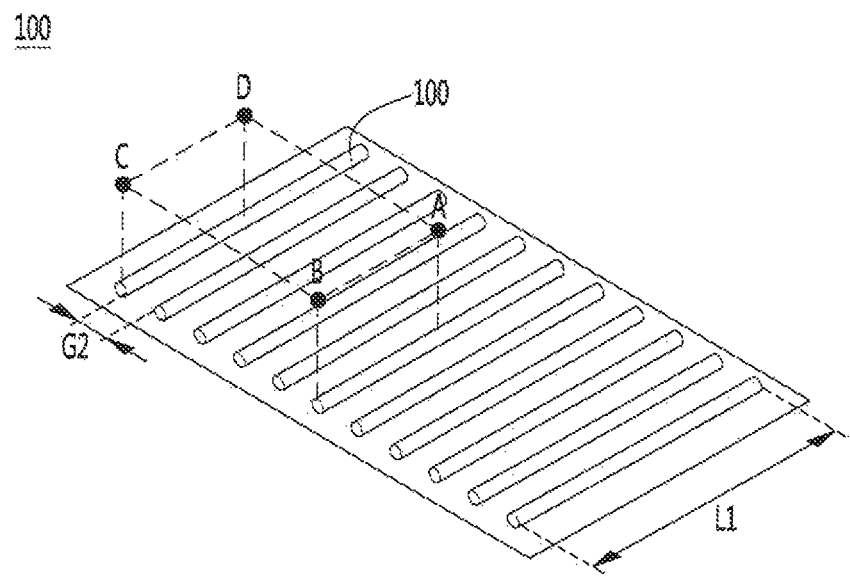
Figure 6C:
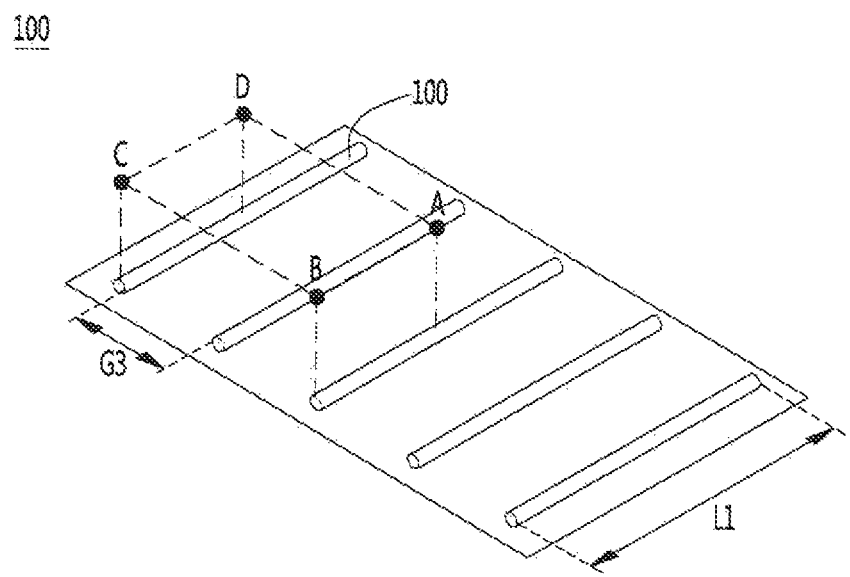
Figure 7A:
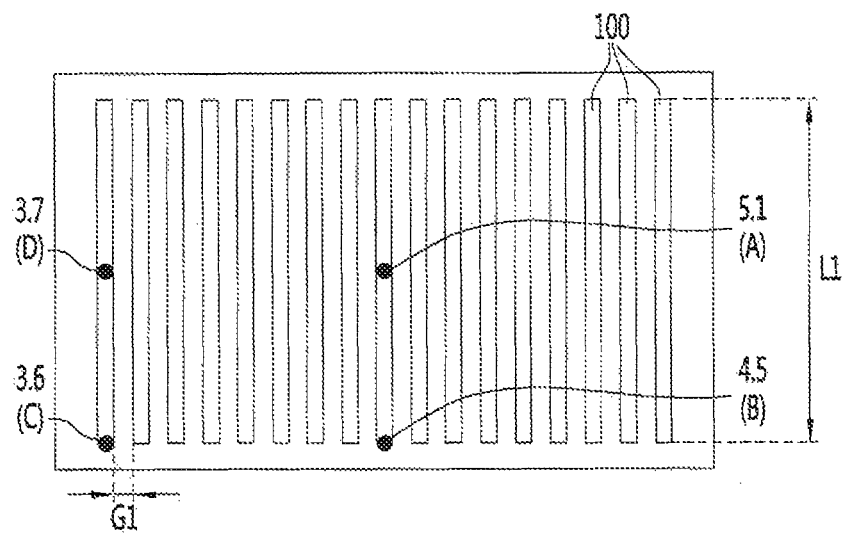
FIGS. 7A-7C are diagrams illustrating power energies measured in FIGS. 6A-6C.
Figure 7B:
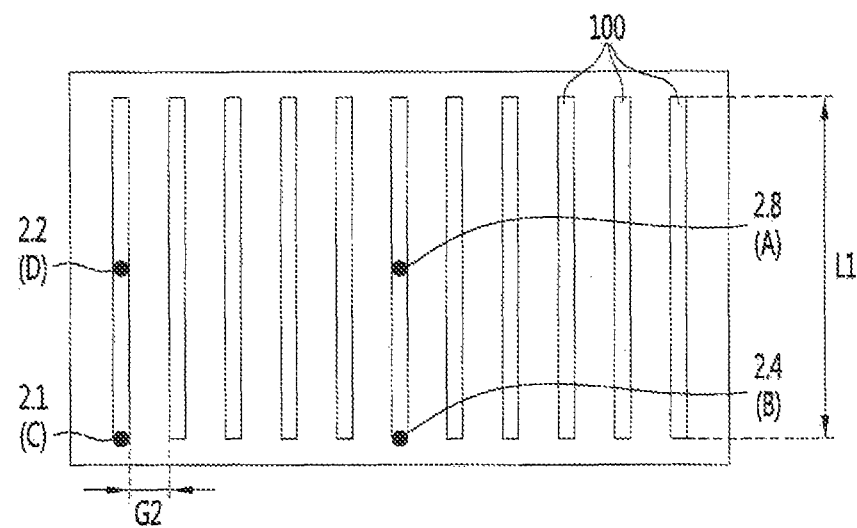
Figure 7C:
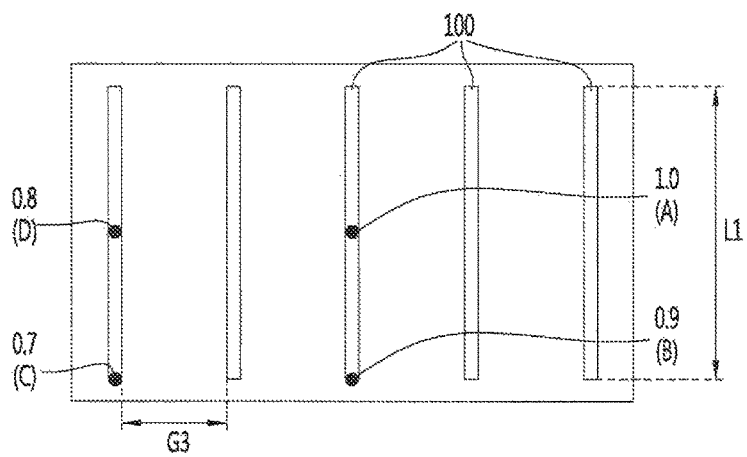

FIGS. 6A-6C are diagrams illustrating power energies measured by changing a spacing between UV sterilization lamps according to an embodiment. FIGS. 7A-7C are diagrams illustrating power energies measured in FIGS. 6A-6C.

Referring to FIGS. 6A-6C and 7A-7C, at least some or all of the plurality of UV sterilization lamps 100 may be arranged in parallel on a constant reference plane. The plurality of UV sterilization lamps 100 may be arranged to be spaced from each other at a constant spacing.

As described above with reference to FIGS. 5A-5C, the plurality of UV sterilization lamps 100 may be formed in a range that does not affect the power consumption and the flow of the fluid, that is, the outer diameter (D1, see FIG. 3) of about 1 mm to about 7 mm and the inner diameter (D2, see FIG. 3) of at least about 0.7 micrometers. The UV rays generated by the plurality of UV sterilization lamps 100 need to be arranged on the constant reference plane so as to be irradiated on the uniform area.

Therefore, FIGS. 6A-6C show power energies of the UV sterilization lamps 100 when the spacing between different UV sterilization lamps 100 is changed. The power energy is energy generated by the UV sterilization lamp 100 and may be understood as an intensity of the UV rays.

The distance between the different UV sterilization lamps 100, that is, the gap G, may be understood as a "length of a tangent line" connecting outer peripheral surfaces of the different UV sterilization lamps 100 at a shortest distance. Further, the gap G may be understood as a "space" or an "area" formed when the tangent line connecting the outer peripheral surfaces of the different UV sterilization lamps 100 at the shortest distance extends in the lengthwise direction of the UV sterilization lamp 100. Further, the gap G may be understood as a length corresponding to a sum of a length of a virtual line connecting centers of the different UV sterilization lamps 100 and a radius of each of the different UV sterilization lamps 100. However, embodiments are not limited thereto.

The inventors measured the intensity of the UV rays when the plurality of UV sterilization lamps 100 is arranged at a same spacing, so as to determine a correlation between a change in the spacing of the UV sterilization lamps 100 and the intensity of the UV rays of the UV sterilization lamp 100. The intensity of the UV rays was measured at a same measurement distance (for example, about 3 cm high).

Further, in order to measure the intensity of the UV rays with respect to the change in the spacing of the UV sterilization lamps 100, the UV sterilization lamps 100 having the same outer diameter (D1 in FIG. 3) and the same inner diameter (D2 in FIG. 3) were provided. The intensity of the UV rays was measured with the UV sterilization lamp 100 which has an inner diameter (D2 in FIG. 3) of about 2 mm, an outer diameter (D1 in FIG. 3) of about 3 mm, a length L1 of about 6 cm, and power consumption of about 2 W per lamp. The power energy per the UV sterilization lamp 100 was measured as about 0.7 mW/cm$^2$.

Referring to FIGS. 6A-6C and 7A, a plurality of UV sterilization lamps 100 may be arranged to be spaced from each other. The plurality of UV sterilization lamps 100 may be arranged to be spaced from each other at a spacing of about 1 cm in a reference space. The distance between different UV sterilization lamps 100 may be referred to as a first gap G1.

The first gap G1 may be provided as about 1 cm, thereby forming a slightly narrow space. As the different UV sterilization lamps 100 are arranged to be close to each other, the UV rays generated by the different UV sterilization lamps 100 may obtain a strong superimposing effect. Due to the superimposing effect, the intensity of the UV rays was measured as a slightly high value. Regarding the superimposing effect, it may be understood that as the plurality of UV sterilization lamps 100 is arranged to be close to each other, the power energies generated by the respective lamps superimpose each other to generate the increased power energy.

Specifically, power energy measured in an A region amounts to about 5.1 mW/cm$^2$; power energy measured in a B region amounts to about 4.5 mW/cm$^2$; power energy measured in a C region amounts to about 3.6 mW/cm$^2$; and power energy measured in a D region amounts to about 3.7 mW/cm$^2$. That is, UV rays having the power energy of about 3.6 mW/cm$^2$ or more may be irradiated in the reference space. The power energy of about 3.6 mW/cm$^2$ is power energy measured in the C region disposed at a distance farthest from the A region.

That is, it can be seen that, as the UV sterilization lamps 100 are arranged to be relatively close to each other, the intensity of the UV rays measured by the superimposing effect is increased. However, as a slightly narrow space is formed between the plurality of UV sterilization lamps 100 arranged at the first gap G1, the fluid which can pass through the first gap G1 may experience flow resistance.

In this case, the fluid passing through the first gap G1 may be partially stagnant by high flow resistance. In other words, the flow velocity of the fluid may be reduced. In the decelerated fluid, the irradiation time of the UV rays may be increased and a strong sterilization may be performed.

On the other hand, when the UV sterilization lamps 100 are arranged at a spacing smaller than the first gap G1 of about 1 cm, a passing distance of the fluid is reduced, thus further increasing flow resistance of the fluid. That is, it becomes difficult for the fluid to pass through the first gap G1. The plurality of UV sterilization lamps 100 arranged with the first gap G1 may act as a single plane. The plurality of UV sterilization lamps 100 may act as a single plane and perform a strong sterilization, but the effect obtained when the fluid passes through the first gap G1 may be reduced. Therefore, the minimum gap proposed according to embodiments is about 1 cm or more.

On the other hand, the first gap G1 may be less than about 1 cm. In this case, the proposed minimum value may be about 0.1 mm or more. The above minimum value is a value that does not consider the flow of the fluid and may be a minimum value for preventing a problem caused by heat generated when different UV sterilization lamps 100 contact each other. However, embodiments are not limited thereto.

Referring to FIGS. 6A-6C and 7B, the plurality of UV sterilization lamps 100 may be arranged to be spaced from each other at a spacing of about 2 cm in the reference space. The distance between different UV sterilization lamps 100 may be referred to as a second gap G2. As the second gap G2 is larger than the first gap G1, the measured power energy is lower than the power energy of the plurality of UV sterilization lamps 100 arranged with the first gap G1.

More specifically, power energy measured in an A region amounts to about 2.8 mW/cm$^2$; power energy measured in a B region amounts to about 2.4 mW/cm$^2$; power energy measured in a C region amounts to about 2.1 mW/cm$^2$; and power energy measured in a D region amounts to about 2.2 mW/cm$^2$. That is, the intensity of the UV rays measured in the case of the second gap G2 is lower than the intensity of the UV rays measured in the case of the first gap G1. On the other hand, as the second gap G2 is larger than the first gap G1, the flow resistance of the fluid passing through the second gap G2 may be reduced.

Therefore, when the plurality of UV sterilization lamps 100 is arranged with the second gap G2, the flow obstruction of the fluid may be reduced. The fluid passing through the second gap G2 may provide a sterilizing power increased by both sides, that is, an inlet side at which the fluid flows into the second gap G2 and an outlet side at which the fluid passes out of the second gap G2.

Referring to FIGS. 6A-6C and 7C, the plurality of UV sterilization lamps 100 may be arranged to be spaced from each other at a spacing of about 8 cm in the reference space. The distance between different UV sterilization lamps 100 may be referred to as a third gap G3. As the third gap G3 is larger than the second gap G2, the measured power energy is lower than the power energy of the plurality of UV sterilization lamps 100 arranged with the second gap G2.

More specifically, power energy measured in an A region amounts to about 1.0 mW/cm$^2$; power energy measured in a B region amounts to about 0.9 mW/cm$^2$; power energy measured in a C region amounts to about 0.7 mW/cm$^2$; and power energy measured in a D region amounts to about 0.8 mW/cm$^2$. That is, the intensity of the UV rays irradiated in the reference space is lower than the intensity of the UV rays measured in the case of the second gap G2. It was confirmed that the superimposing effect was reduced from the third gap G3.

Further, as the third gap G3 is larger than the second gap G2, the flow resistance of the fluid passing through the third gap G3 may be slight. Therefore, when the plurality of UV sterilization lamps 100 is arranged with the third gap G3, it does not affect the flow of the fluid flowing through the third gap G3. However, as the intensity of the UV rays is slight, it may be difficult to obtain a strong sterilization.

As a result, the gap G of the different UV sterilization lamps 100, which is proposed in this embodiment, may be about 1 cm to about 8 cm. The gap G may have a relationship inversely proportional to the intensity of the UV rays.

On the other hand, the different UV sterilization lamps 100 proposed in this embodiment aim to perform uniform sterilization with the same outer diameter D1, but when a strong sterilization is wanted in a specific region instead of uniform sterilization, the UV sterilization lamps 100 may be formed to have different outer diameters. For example, the plurality of first UV sterilization lamps (100*a* in FIGS. 5A-5C) having the first outer diameter (D1*a* in FIGS. 5A-5C) may be arranged with a desirable gap G. The second UV sterilization lamps (100*b* in FIGS. 5A-5C) having the second outer diameter (D1*b* in FIGS. 5A-5C) may be arranged between the plurality of first UV sterilization lamps (100*a* in FIGS. 5A-5C) so as to further increase the intensity of the UV rays in the specific region. According to this configuration, the intensity of the UV rays in the region where the second UV sterilization lamps 100*b* are arranged may be further increased. However, embodiments are not limited thereto.

Figure 8:
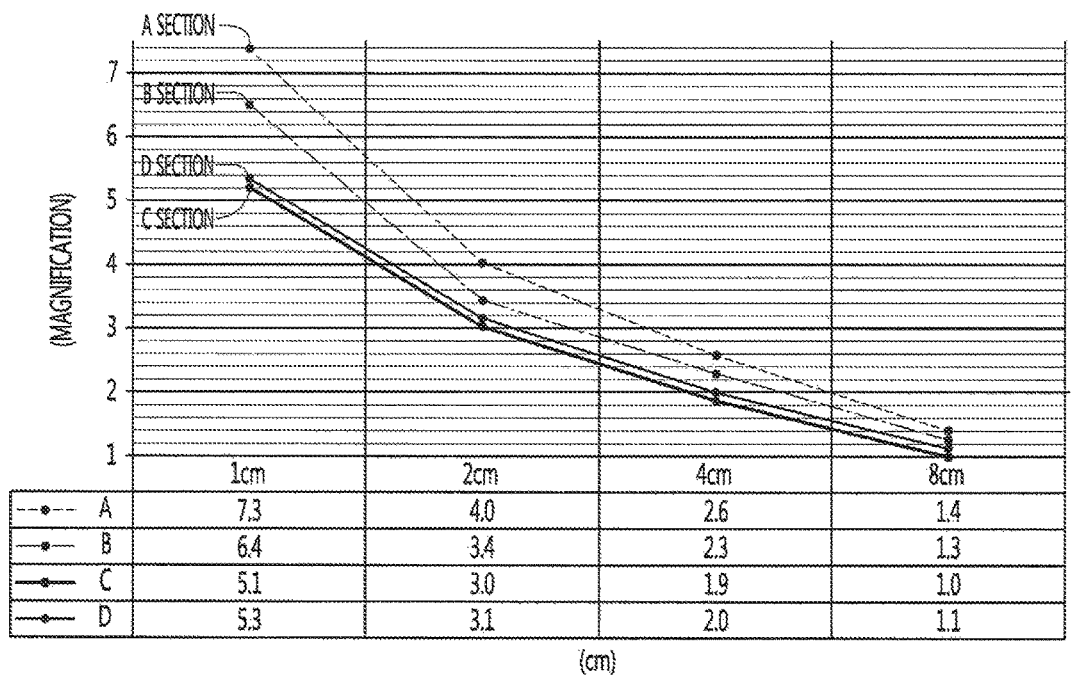
FIG. 8 is a graph showing comparison between power energies measured for each spacing in FIGS. 6A-6C and 7A-7C and reference power energy.

FIG. 8 is a graph showing comparison between power energies measured for each spacing in FIGS. 6A-6C and 7A-7C and reference power energy. Referring to FIG. 8, the power energies measured in the A, B, C, and D sections are compared with the power energy measured at the single UV sterilization lamp 100 (hereinafter, referred to as "reference power energy"). The reference power energy is power energy measured at the single UV sterilization lamp 100, and it is assumed as about 0.7 mW/cm$^2$.

The Y axis represents a value obtained by dividing the measured power energy by the reference power energy, and the measured power energy is higher in magnification than the reference power energy. The X axis represents a magnification changed for each gap.

Referring to the graph, the values of the power energies, that is, the Intensities of the UV rays, were measured to be higher in order of the A section, the B section, the D section, and the C section. In other words, it can be seen that the power energy is lowest in the C section farthest from the A section.

Therefore, in this embodiment, the power energy measured in the C section may be considered to be the minimum intensity of the UV rays generated in the reference space. Further, the optimal gap G capable of obtaining the superimposing effect may be determined according to whether the superimposing effect affects the power energy measured in the C section.

More specifically, the power energy of the C section measured with the minimum gap of about 1 cm proposed in this embodiment was about 4.8 times the reference power energy. In other words, when different UV sterilization lamps 100 are provided with the spacing of about 1 cm, the UV rays having about 4.8 times higher intensity than that in the case of using the single UV sterilization lamp 100.

It can be confirmed that as the gap G increases, magnification of the measured power energy and the reference power energy is gradually reduced. The power energy of the C section measured with the maximum gap of about 8 cm proposed in this embodiment was the same as the reference power energy. In other words, the superimposing effect is slight when the plurality of UV sterilization lamps 100 are arranged with a gap greater than the maximum gap proposed in this embodiment. As a result, as the gap G between different UV sterilization lamps 100 is reduced, the flow resistance of the fluid passing through the gap G and the intensity of the UV rays may be increased in inverse proportion.

According to this configuration, the efficiency of the superimposing effect may be maximized when the plurality of UV sterilization lamps 100 according to this embodiment is arranged with the maximum gap of about 8 cm. Further, the sterilizing effect of the fluid passing through the gap G may also be maximized. Further, the plurality of UV sterilization lamps 100 may perform uniform sterilization in an entire region from the central region (A region) to the farthest external region (C region).

Another embodiment is disclosed hereinafter. With this embodiment, the UV sterilization lamps of the previous embodiment are provided as a single UV sterilization module. Therefore, in this embodiment, descriptions of the previous embodiment may be applied to the same parts as those of the previous embodiment.

Figure 9:
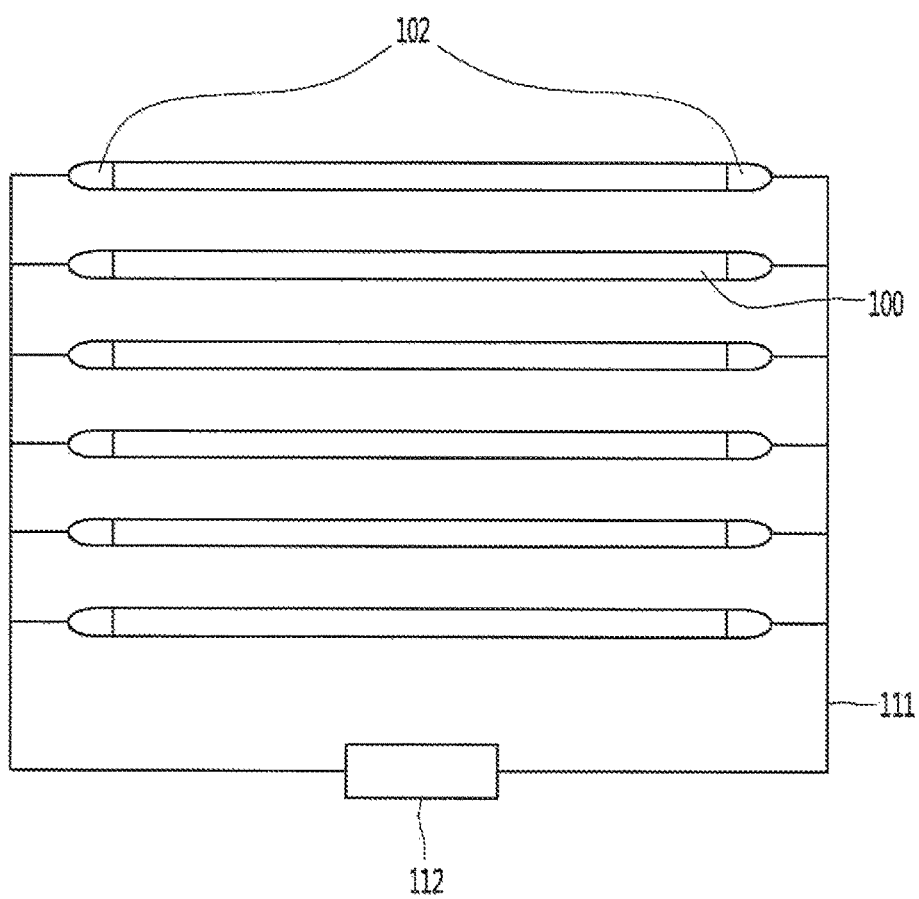
FIG. 9 is a schematic diagram of a UV sterilization module according to an embodiment.

FIG. 9 is a schematic diagram of a UV sterilization module according to an embodiment. Referring to FIG. 9, the UV sterilization module 110 according to this embodiment may include a plurality of UV sterilization lamps 100 arranged to be spaced from each other, an electrical line 111 connected to the plurality of UV sterilization lamps 100, and a power supply 112 connected to the electrical line 111.

The electrical line 111 may be connected to the external electrode unit (102 in FIG. 1) of the UV sterilization lamp 100. For example, the electrical line 111 may be directly connected to the external electrode unit 102 by soldering, or an adhesive, for example. The electrical line 111 may be connected in parallel to the plurality of UV sterilization lamps 100 and the power supply 112. However, embodiments are not limited thereto, and the electrical line 111 may be connected in series to the plurality of UV sterilization lamps 100 and the power supply 112. However, in this embodiment, the parallel connection is presented so as to reduce a size of the plurality of UV sterilization lamps 100 and power consumption.

The power supply 112 may supply power to each UV sterilization lamp 100. The power supply 112 may stabilize current to be supplied to the UV sterilization lamp 100 and supply the stabilized current to the UV sterilization lamp 100. Further, the power supply 112 may generate a high voltage required for generating the UV rays in the UV sterilization lamp 100.

For example, the power supply 112 may be an apparatus for stabilizing the power to be supplied to the UV sterilization lamp 100, that is, a stabilizer, or an inverter, for example. Further, the power supply 112 may be provided such that a power system for receiving power from the outside is separated from an apparatus for stabilizing the power to be supplied to the UV sterilization lamp 100. However, embodiments are not limited thereto.

That is, the power supply 122 may be configured to change an output frequency and drive voltage based on a drive frequency and drive voltage required for driving the plurality of UV sterilization lamps 100. Therefore, the power supply 112 may be any device that can supply power so as to drive the plurality of UV sterilization lamps 100.

As a result, the parallel connection between the power supply 112 and the plurality of UV sterilization lamps 100 may allow the plurality of UV sterilization lamps 100 to turn on concurrently. Further, the power supply 112 may supply a high voltage and a low current required in the plurality of UV sterilization lamps 100. Further, when the plurality of UV sterilization lamps 100 include a defective UV sterilization lamp 100, the defective UV sterilization lamp 100 may be simply replaced Another embodiment is disclosed hereinafter. In this embodiment, a body is provided that supports the UV sterilization module in the previous embodiment. Therefore, in this embodiment, descriptions of the previous embodiment may be applied to the same parts as those of the previous embodiment.

Figure 10:
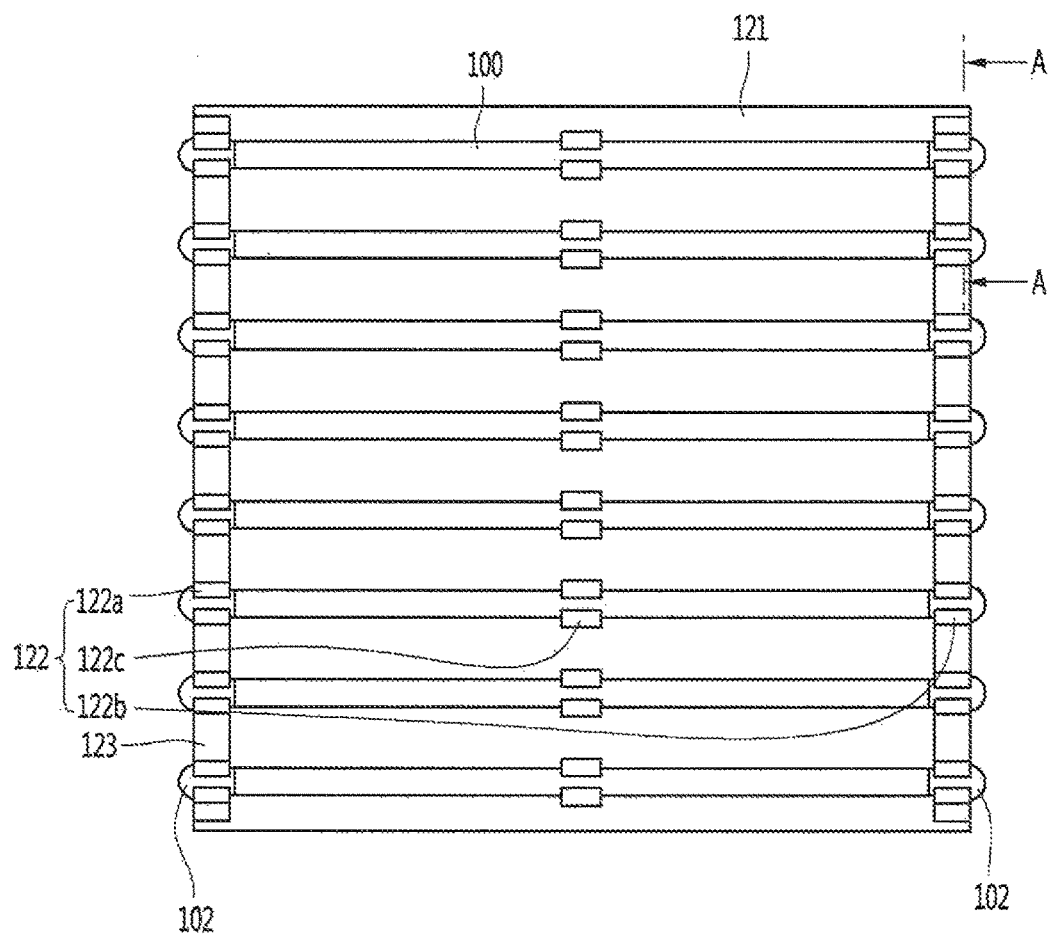
FIG. 10 is a plan view of a UV sterilization module according to another embodiment.
Figure 11:
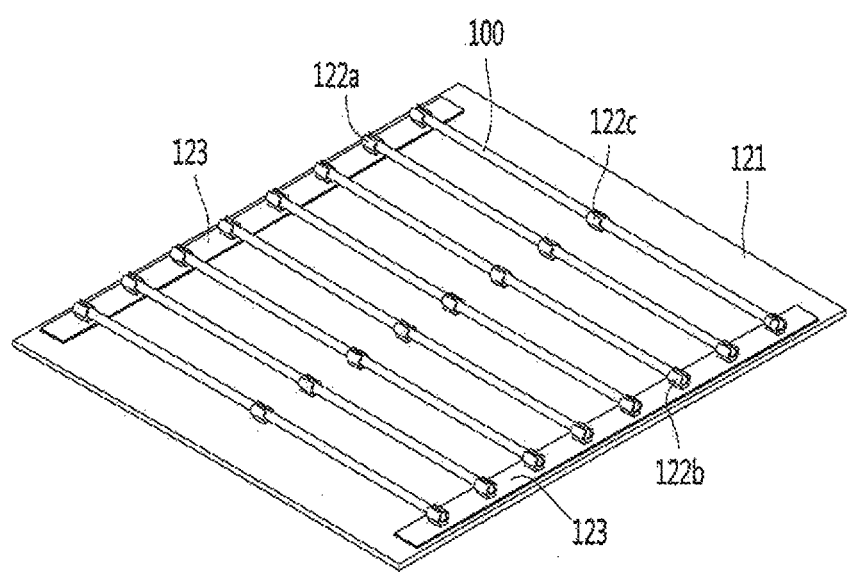
FIG. 11 is a perspective view of the UV sterilization module of FIG. 10.
Figure 12:
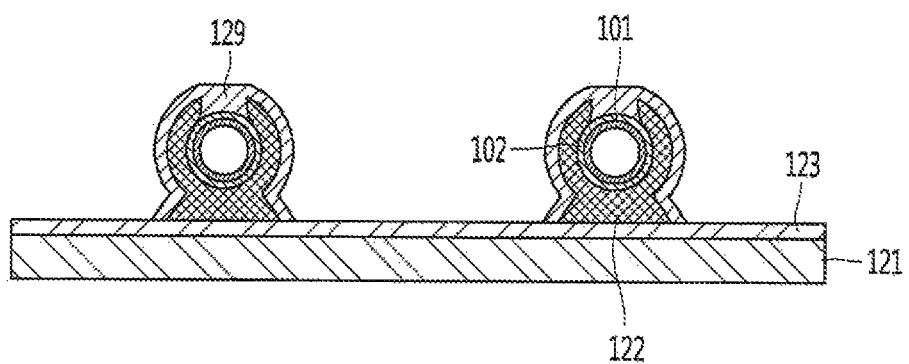
FIG. 12 is a cross-sectional view taken along line XII-XII in the UV sterilization module of FIG. 10.

FIG. 10 is a plan view of a UV sterilization module according to another embodiment. FIG. 11 is a perspective view of the UV sterilization module of FIG. 10. FIG. 12 is a cross-sectional view taken along line XII-XII in the UV sterilization module of FIG. 10.

Referring to FIGS. 10 to 12, the UV sterilization module 120 according to this embodiment may include a plurality of UV sterilization lamps 100 arranged to be spaced from each other, a module body 121 configured to support the plurality of UV sterilization lamps 100, and a fixing portion 122 disposed or provided between the plurality of UV sterilization lamps 100 and the module body 121. The UV sterilization module 120 may further include a power supply (112, see FIG. 9) and an electrical line (111, see FIG. 9) configured to supply power to the plurality of UV sterilization lamps 100.

The fixing portion 122 may be formed to surround a portion of an outer peripheral surface of the UV sterilization lamp 100. A plurality of the fixing portion 122 may be provided. For example, the fixing portion 122 may be a holder, a hook, or a clip, for example. The fixing portion 122 may be fixed to the module body 121 to be described hereinafter. Further, the plurality of fixing portions 122 may be the same as each other such that the UV sterilization lamps 100 are arranged in parallel.

The fixing portions 122 may support both sides of the UV sterilization lamp 100. Further, the fixing portions 122 may be respectively provided at both sides, that is, first and second or left and right sides of the UV sterilization lamp 100, and may also be provided in a center portion between the left and right sides.

The fixing portion 122 may be made of at least one of a conductive material or a non-conductive material. Further, the fixing portion 122 may be made of an elastic material so as to easily support outer peripheral surfaces of both sides of the UV sterilization lamp 100. When the fixing portion 122 is made of an elastic material, the UV sterilization lamp 100 may be easily detached or attached.

That is, the fixing portion 122 may be provided on the outer peripheral surfaces of both sides of the UV sterilization lamp 100 so as to fix the UV sterilization lamp 100. When the fixing portion 122 is made of a conductive material, the fixing portion 122 may serve to supply power to the UV sterilization lamp 100.

For example, the fixing portion 122 may be disposed or provided on each of the first electrode unit 102a and the second electrode unit 102b of the UV sterilization lamp 100. The fixing portion 122 may also be disposed or provided in the center portion of the UV sterilization lamp 100. The fixing portion 122 disposed or provided in the first electrode unit 102a may be referred to as a first fixing portion 122a. The fixing portion 122 disposed or provided in the second electrode unit 102b may be referred to as a second fixing portion 122b. The fixing portion 122 disposed or provided in the center portion may be referred to as a third fixing portion 122c. The first fixing portion 122a and the second fixing portion 122b may be made of a conductive material. The third fixing portion 122c may be made of a non-conductive material. As the first fixing portion 122a and the second fixing portion 122b may be made of the conductive material, and thus, may apply power, the first fixing portion 122a and the second fixing portion 122b may be referred to as a "conductive fixing portion". As the third fixing portions 122c supports the weight of the UV sterilization lamp 100, the third fixing portion 122c may be referred to as a "support fixing portion". However, embodiments are not limited thereto.

The fixing portion 122 may be fixed to the module body 121. Further, the fixing portion 122 may be detachably coupled to the module body 121. That is, the plurality of UV sterilization lamps 100 may be supported by the module body 121 via the fixing portion 122.

The module body 121 may be formed to have a constant width and a constant length. The length of the module body 121 may be smaller than the width of the module body 121. The UV sterilization lamps 100 may be arranged in the widthwise direction of the module body 121. The UV sterilization lamp 100 may be smaller than the width of the module body 121. The UV sterilization lamps 100 may be arranged to be spaced from each other in the lengthwise direction of the module body 121. The UV sterilization lamps 100 may be arranged to be spaced from each other in the lengthwise direction of the module body 121, and a number of UV sterilization lamps 100 may be determined accordingly.

The module body 121 may be a board or a frame that supports the fixing portion 122 and the UV sterilization lamp 100. The module body 121 may be formed to have a constant flexibility or elasticity. For example, the module body 121 may be a flexible printed circuit board (FPCB) which has flexibility and elasticity and may form an electrical circuit. When the FPCB is provided as the module body 121, the module body 121 may be deformed to be disposed or provided in various spaces in a state of supporting the fixing portion 122 and the UV sterilization lamp 100.

The module body 121 may include an electrode rail 123 that allows power to be supplied to the UV sterilization lamp 100 through the fixing portion 122. The electrode rail 123 may be provided on an outer surface of the module body 121. Further, the electrode rail 123 may be provided inside of the module body 121. In this case, as the fixing portion 122 may contact the electrode rail 123, the fixing portion 122 may pass through a portion of the module body 121. However, embodiments are not limited thereto. In this embodiment, it is assumed that the electrode rail 123 is provided on the outer surface of the module body 121.

The plurality of fixing portions 122 may be disposed or provided on the electrode rail 123. The plurality of fixing portions 122 may be arranged to be spaced from each other. The electrode rail 123 may be connected to the power supply (112, see FIG. 9) and the electrical line (111, see FIG. 9). That is, the fixing portions 122, that is, the conductive fixing portions 122*a* and 122*b*, may be fixed to the electrode rail 123, and thus, the power may be supplied to the UV sterilization lamp 100.

A sealing portion 129 may be provided in or on the lamp body 121. The sealing portion 129 may prevent water drops, for example, from penetrating into a portion where the power is applied to the UV sterilization lamp 100. Therefore, the sealing portion 129 may include a water-proof material. Further, the sealing portion 129 may include an insulating material.

The sealing portion 129 may be provided in or on the electrode rail 123, the conductive fixing portions 122*a* and 122*b*, and the external electrode unit 102 of the UV sterilization lamp. Further, the sealing portion 129 may be provided in or on a portion of the conductive fixing portions 122*a* and 122*b* and the external electrode unit 102. However, embodiments are not limited thereto. In this embodiment, the sealing portion 129 is illustrated as being provided in or on only the conductive fixing portions 122*a* and 122*b* and the external electrode unit 102.

According to this configuration, the sealing portion 129 may prevent occurrence of safety accidents due to moisture or electrical short circuit. Further, the sealing portion 129 may prevent the UV sterilization lamp 100 from being separated from the fixing portion 122.

Still another embodiment is disclosed hereinafter. In this embodiment, a portion of the body that supports the UV sterilization module of the previous embodiment is deformed. Therefore, in this embodiment, descriptions of the previous embodiment may be applied to the same parts as those of the previous embodiment.

Figure 13:
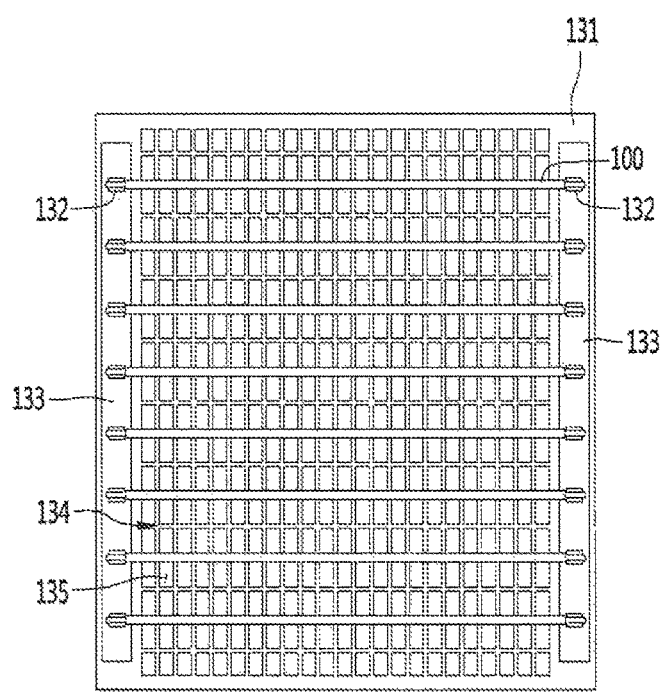
FIG. 13 is a plan view of a UV sterilization module according to still another embodiment.
Figure 14:
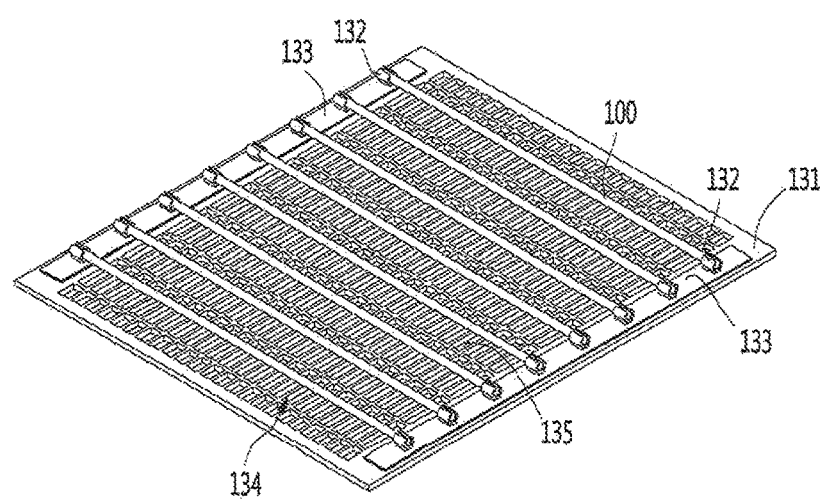
FIG. 14 is a perspective view of the UV sterilization module of FIG. 13.

FIG. 13 is a plan view of a UV sterilization module according to still another embodiment. FIG. 14 is a perspective view of the UV sterilization module of FIG. 13.

Referring to FIGS. 13 and 14, the UV sterilization module 130 according to this embodiment may include a plurality of UV sterilization lamps 100, a fixing portion 132 configured to support the plurality of UV sterilization lamps 100, a module body 131 configured to support the fixing portion 132, and a porous portion 134 provided in the module body 131. The UV sterilization module 130 may further include a power supply (112, see FIG. 9) and an electrical line (111, see FIG. 9) configured to supply power to the plurality of UV sterilization lamps 100.

The module body 131 may be formed to have a constant width and a constant length. The length of the module body 131 may be smaller than the width of the module body 131. The UV sterilization lamps 100 may be arranged in the widthwise direction of the module body 131. The UV sterilization lamp 100 may be smaller than the width of the module body 131. The UV sterilization lamps 100 may be arranged to be spaced from each other in the lengthwise direction of the module body 131. The UV sterilization lamps 100 may be arranged to be spaced from each other in the lengthwise direction of the module body 131, and a number of UV sterilization lamps 100 may be determined accordingly.

The module body 131 may be made of a material having a constant flexibility or elasticity. The module body 131 may be made of a material having high durability with respect to at least heat and humidity. The module body 131 may be partially a mesh or have a mesh shape, instead of the FPCB described in the previous embodiment. A portion of the module body 131 provided in the mesh or net shape may be made of at least aluminum (Al), for example. The module body 131 including the porous portion 134 may be referred to as a "porous frame".

That is, the porous portion 134 may be understood as a region formed by a plurality of holes 135 in a portion of the module body. The porous portion 134 may be provided by the plurality of holes 135 formed by a plurality of wires intersecting with each other. Further, the porous portion 134 may pass through the plurality of holes 135 in the module body 131. Further, a separate mesh may be provided as the porous portion 134. In the module body 131 having a hollow region, the porous portion 134 may be coupled to the hollow region. However, embodiments are not limited thereto.

That is, as the porous portion 134 may be provided in the module body 131, the UV rays generated by the UV sterilization lamp 100 may be irradiated in all directions. Further, a passage through which the fluid may flow may be formed through the porous portion 134. In other words, the fluid to be sterilized may pass through the porous portion 134. Further, while the fluid passes through the porous portion 134, the irradiation area of the UV rays, and the irradiation intensity of the UV rays, for example, may be increased. Thus, the sterilizing power by the UV sterilization lamp 100 may be increased.

The hole 135 may be formed to have various shapes, such as a circular shape, a polygonal shape, or an oval shape, for example. Further, a size of the hole 135 may affect the flow of the fluid which can pass through the porous portion 134. Therefore, a flow rate passing through the module body 131 may be adjusted according to a change in the size of the hole 135.

Further, a photocatalyst coating may be applied on the module body 131 where the porous portion 134 is formed. When the photocatalyst coating is applied on the module body 131, the fluid passing through the porous portion 134 may obtain a deodorizing effect by the photocatalyst coating. For example, the photocatalyst coating may include a $TiO_2$, ZnO, CdS, $ZrO_2$, $V_2O_3$, or $WO_3$ coating, etc, for example. That is, the fluid may obtain a deodorizing effect as well as a sterilizing effect by the UV sterilization lamp 100.

Another embodiment is disclosed hereinafter. With this embodiment, the UV sterilization lamp and the UV sterilization module proposed in the previous embodiments are arranged inside of an air conditioner, for example, a wall-mounted air conditioner. Therefore, in this embodiment, the descriptions of the previous embodiments may be applied to the same parts as those of the previous embodiments.

Figure 15:
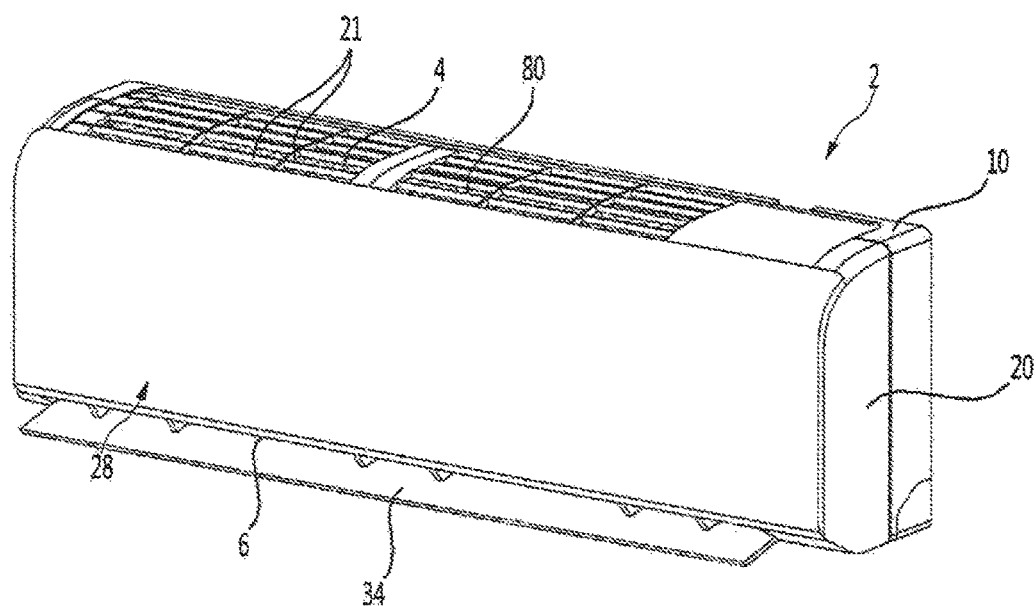
FIG. 15 is a perspective view of an air conditioner (wall-mounted air conditioner) according to an embodiment, during an operation.
Figure 16:
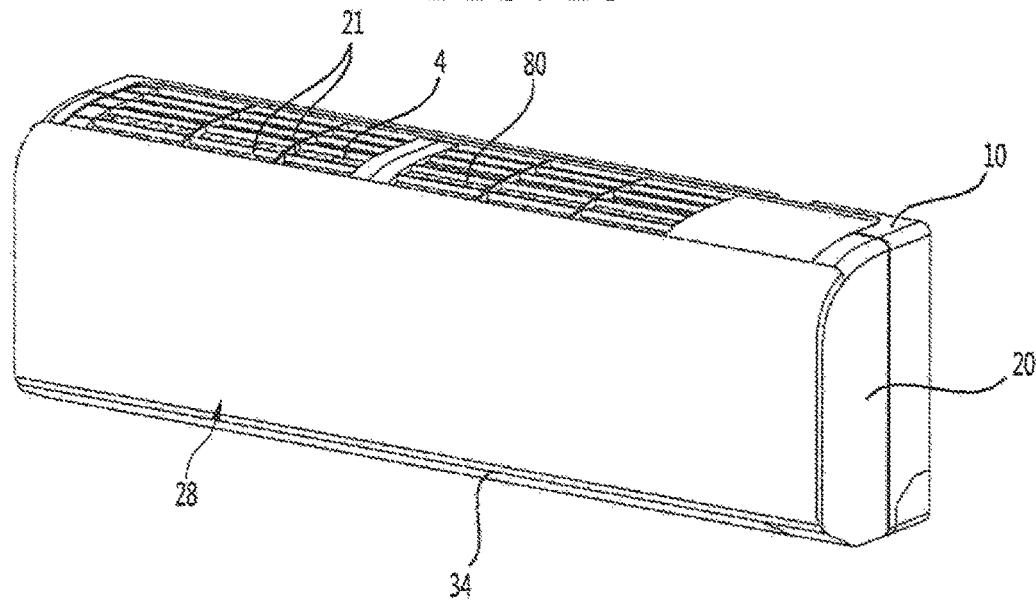
FIG. 16 is a perspective view of the air conditioner (wall-mounted air conditioner) of FIG. 15 during an operation stop.
Figure 17:
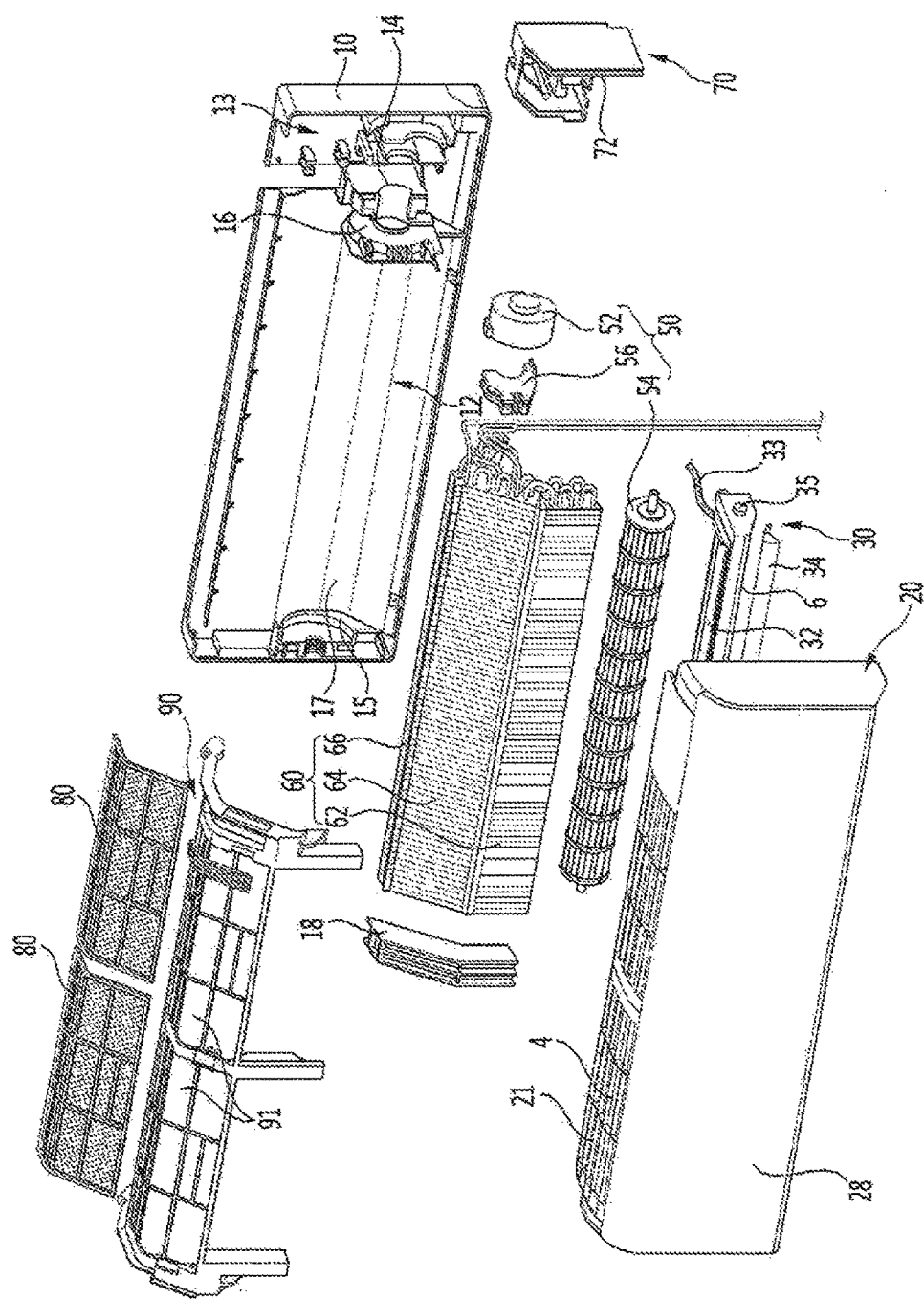
FIG. 17 is an exploded perspective view of the air conditioner (wall-mounted air conditioner) of FIG. 15.
Figure 18:
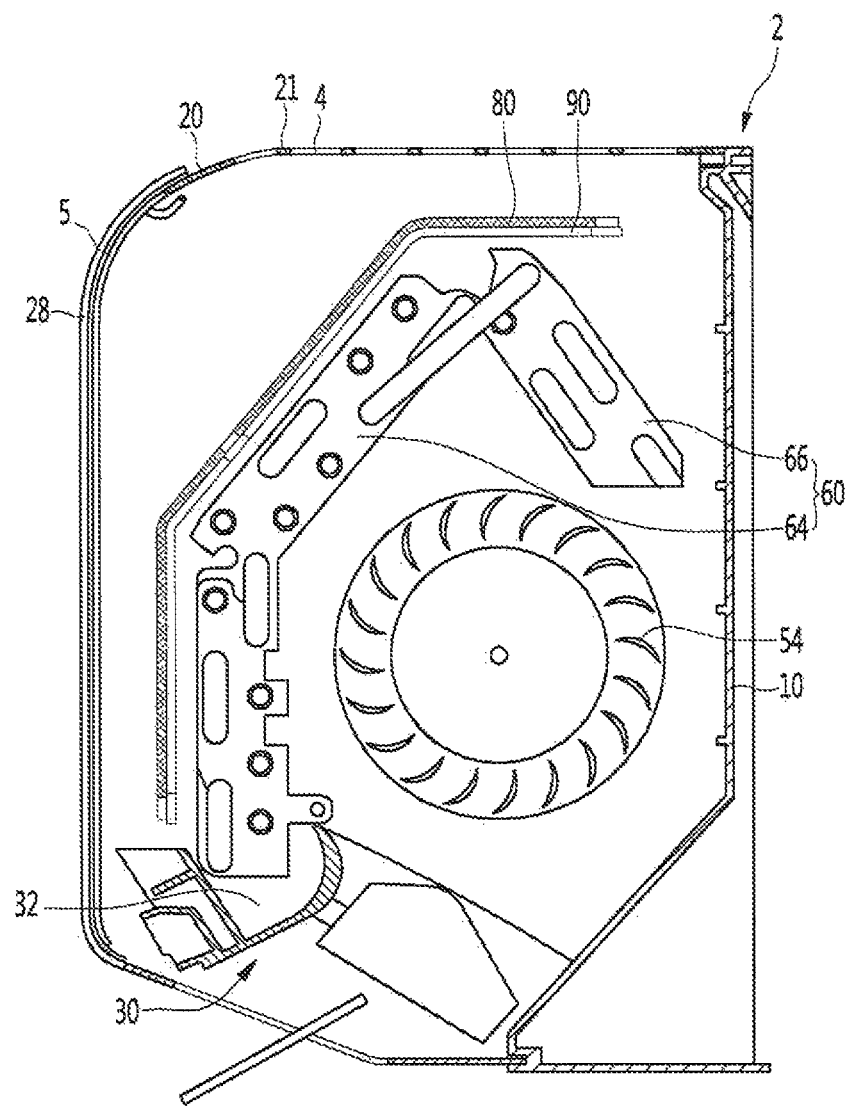
FIG. 18 is a vertical cross-sectional view for describing a state when a wind-direction adjustment member in FIG. 15 discharges and guides conditioned air to an indoor space.

FIG. 15 is a perspective view of an air conditioner (wall-mounted air conditioner) according to an embodiment during an operation. FIG. 16 is a perspective view of the air conditioner (wall-mounted air conditioner) of FIG. 15 during an operation stop. FIG. 17 is an exploded perspective view of the air conditioner (wall-mounted air conditioner) of FIG. 15. FIG. 18 is a vertical cross-sectional view for describing a state when a wind-direction adjustment member in FIG. 15 discharges and guides conditioned air to an indoor space.

Figure 19:
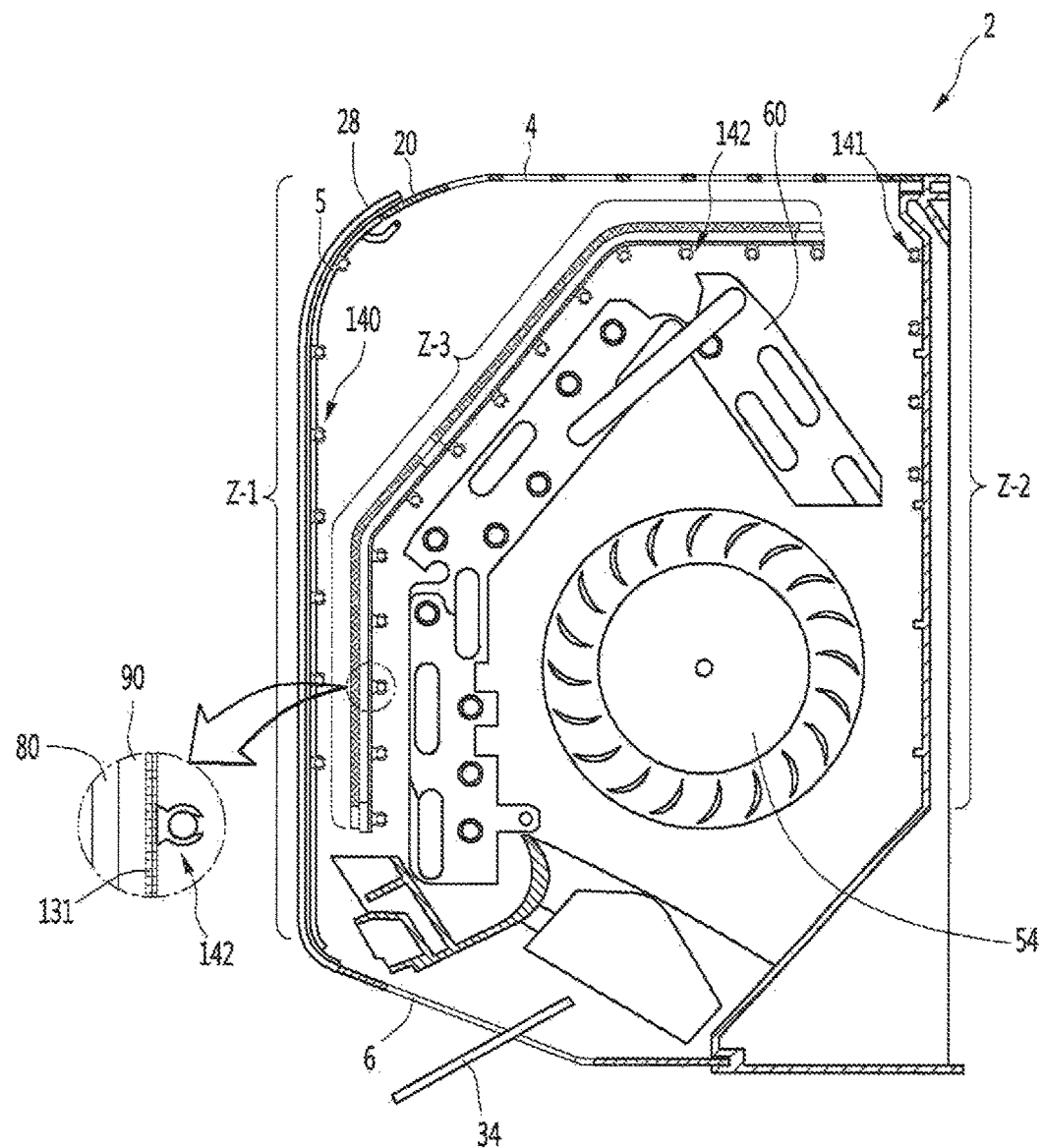
FIG. 19 is a vertical cross-sectional view of an air conditioner (wall-mounted air conditioner) including a UV sterilization module according to yet another embodiment.
Figure 20:
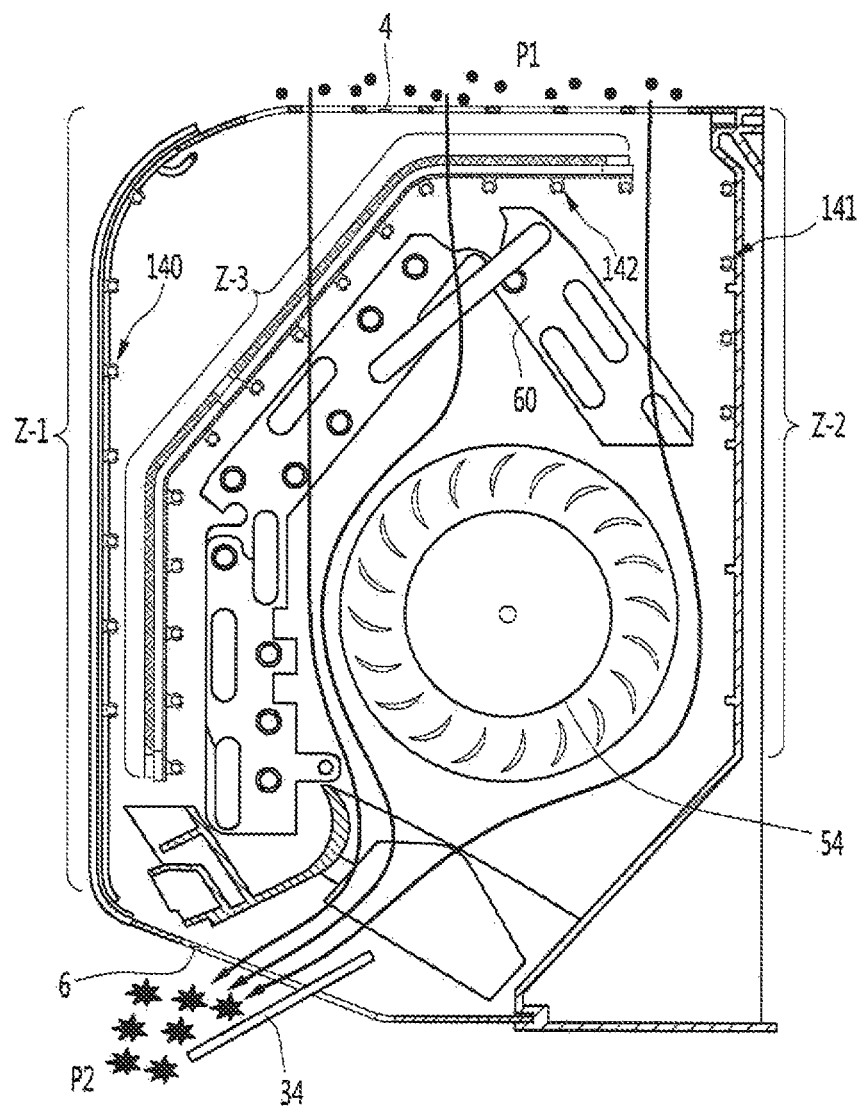
FIG. 20 is a diagram illustrating a sterilizing operation of the UV sterilization module of FIG. 19.

FIG. 19 is a vertical cross-sectional view of an air conditioner (wall-mounted air conditioner) including a UV sterilization module according to yet another embodiment. FIG. 20 is a diagram illustrating a sterilizing operation of the UV sterilization module of FIG. 19.

Referring to FIGS. 15 to 18, the air conditioner may include a main body 2 having an air inlet 4 to receive indoor air and an air outlet 6 to discharge conditioned air. The air conditioner may be configured to receive air from the air inlet 4 and to condition the air therein and then to discharge the conditioned air via the air outlet 6. The air conditioner may be implemented as a stand-type air conditioner, a ceil-mounted air conditioner, or a wall-mounted air conditioner, for example. Hereinafter, a reference may be made to a wall-mounted air conditioner by way of example.

The main body 2 may be installed indoors and may be a singular component or a combination of multiple members. In the latter case, the main body 2 may include a chassis 10, a front frame 20, an absorption grill 21, a front panel 28, and a discharge unit or device 30.

In the main body 2, the air inlet 4 may be formed in front and top portions thereof and the air outlet 6 may be formed in a bottom portion thereof. The front panel 28 may move in a front-rear direction or may pivot downward or upward to form an air absorption channel between a front surface and the front panel 28.

Alternatively, in the main body 2, the air inlet 4 may be formed in a top portion thereof and the air outlet 6 may be formed in a bottom portion thereof. The main body 2 may have an opening for maintenance of the air conditioner at the front portion thereof, and the front panel 28 may be arranged to open and close the front surface and the opening of the main body 2.

Hereinafter, a reference will be made to an example where the air inlet 4 is formed at a top portion of the main body 2, and the air outlet 6 is formed at a bottom portion of the main body 2. The front panel 28 may form a front appearance of the air conditioner and may be configured to pivot around an upper edge thereof or to move in a front-rear direction.

The chassis 10 may be mounted to a wall and may define an air flow channel therein. The chassis 10 may be function as a housing to receive various components.

The chassis 10 may have a wind channel guide 12 formed therein to guide an air from the air inlet 4 to the air outlet 6. At one of left and right sides of the wind channel guide 12, an electronics board 13 may be disposed on which various electronic components may be mounted.

The wind channel guide 12 may define an air channel for a fan 54 as described hereinafter. The wind channel guide 12 may include left and right or first and second guides 15, 16 the expand in a frontward direction from the chassis 10, and a middle guide 17 between the left and right guides 15, 16. At one of the left and right guides 15,16, a heat exchanger supporter 18 may be disposed or provided to support the heat exchanger 60 and to define an air channel. From the electronics board 13, a motor installation 14 may protrude in a frontward direction to receive a fan motor 52. On the electronics board 13, a control box 70 may be disposed or provided to control the air conditioner. The control box 70 may be disposed or provided together with a controller (not shown) for the fan motor 52 of an air blower 50 and a wind-direction adjustment member driver 35, for example.

The front frame 20 may be provided at a front of the chassis 10 to define a space with the chassis 10. The front frame 20 may define a wind channel with the wind channel guide 12 of the chassis 10, and may cover the electronics board 13 on the chassis 10 to protect the electronics board 13. The front frame 20 may have openings in top and front portions thereof. The opening in the top portion may act as the air inlet 4. The front opening 5 may act as an access passage to maintain the filter 80 or the UV sterilization module according to embodiments.

The front frame 20 may have the front opening 5 in front of the wind channel guide 12 of the chassis 10. An upper opening may be formed at an upper portion in front of the wind channel guide 12 of the chassis 10.

The absorption grill 21 may allow indoor air to be suctioned into the main body 2 and may protect a bottom of the body. The absorption grill 21 may be formed in a grill shape on the upper opening of the front frame 20.

The discharge unit 30 may discharge conditioned air out of the main body 2. The discharge unit 30 may be assembled to at least one of the chassis 10 on the front frame 20 via a fastener or a hook.

On top of the discharge unit 30, a drain 32 may be provided to collect condensed water falling from a heat exchanger 60. The drain 32 may be coupled to a drain connection hose 33 to guide the condensed water out of the main body 2. The air outlet 6 may be formed on the bottom of the drain 32.

The discharge unit 30 may have a wind-direction adjuster to control a wind-direction of air passing through the air outlet 6. The wind-direction adjuster may guide the air passing through the air outlet 6 and control the wind-direction. To this end, the wind-direction adjuster may include a wind-direction adjustment member 34 rotatably disposed or provided at the main body 2, more particularly, at the discharge unit 30, and the wind-direction adjustment member driver 35 to rotate the wind-direction adjustment member 34.

The wind-direction adjustment member 34 may include a horizontal wind-direction adjustment member to control a horizontal wind-direction of the air passing through the air outlet 6, and a vertical wind-direction adjustment member to control a vertical wind-direction of the air passing through the air outlet 6. The wind-direction adjustment member driver 35 may be coupled to the horizontal wind-direction adjustment member to allow the horizontal wind-direction adjustment member to rotate around a vertical axis. Further, the wind-direction adjustment member driver 35 may be coupled to the vertical wind-direction adjustment member to allow the vertical wind-direction adjustment member to rotate around a horizontal axis.

The wind-direction adjustment member 34 may rotate to allow one of the horizontal wind-direction adjustment member or vertical wind-direction adjustment member to open or close the air outlet 6. Hereinafter, reference will be made to a configuration where the vertical wind-direction adjustment member closes or opens the air outlet 6, the wind-direction adjustment member driver 35 is provided at one of left and right or first and second sides of the discharge unit 30 to drive the rotation of the vertical wind-direction adjustment member as a wind-direction adjustment motor.

The main body 2 may receive the air blower 50 to suction the air into the air inlet 4 and move the air into the main body 2 and discharge the air to the air outlet 6. Further, the main body 2 may receive the heat exchanger 60 to allow heat exchange between the air and a refrigerant. Further, the main body 2 may receive the filter 80 to purify the air absorbed into the air inlet 4 and a filter frame 90 for the filter 80.

The air blower 50 may include the fan motor 52 supported by in the motor installation 14 formed in the chassis 10, more particularly, the electronics board 13, and the fan 54 disposed or provided at a rotation axis of the fan motor 52 and located on the wind channel guide 12. The fan 54 may be implemented as a horizontally-elongated cross flow fan between the wind channel guides 15,16,17, more particularly, between the left and right channel guides 15,16. The air blower 50 may further include a motor cover 56 disposed or provided at the chassis 10 to cover the fan motor 52.

The heat exchanger 60 may be located between the air inlet 4 and the fan 54. The heat exchanger 60 may be located in a rear of the front frame 20 and may have a lower end disposed on top of the drain 32. The heat exchanger 60 may include a vertical portion 62 on a top of the drain 32, a front tilted portion 64 from a top of the vertical portion 62 to a top of a rear portion, and a rear tilted portion 66 from a top of the front tilted portion 64 to a bottom of a rear portion.

The filter frame 90 may be provided between the air inlet 4 and the heat exchanger 60. The filter frame 90 may have openings 91 formed therein to receive the filter 80.

In this embodiment, the air conditioner may include a controller (not shown) provided in the main body 2 to control the fan motor 52 and the wind-direction adjustment member driver 35, for example. The controller may control the fan motor 52 and wind-direction adjustment member driver 35 during an air cooling operation. Cool conditioned air may be guided to the wind-direction adjustment member 34 and then be discharged therefrom. The wind-direction adjustment member 34 may spread the conditioned air via a rotation thereof. In an opening mode of the wind-direction adjustment member driver 35, the wind-direction adjustment member 34 may open the air outlet 6 via a rotation of the wind-direction adjustment member driver 35. The rotation of the fan motor 52 may rotate the fan 54. The rotation of the fan 54 may allow the indoor air to be suctioned via the air inlet 4 into the main body 2 and then to be purified via the filter 80 and then to have a heat exchange with the heat exchanger 60. Then, the air may pass through the air outlet 6 and then lead to the wind-direction adjustment member 34 and then be discharged therefrom.

In a swing discharge mode, the controller may allow forward/reverse rotations of the wind-direction adjustment member driver 35 during the rotation of the fan motor 52. Further, the wind-direction adjustment member 34 may translate vertically via the wind-direction adjustment member driver 35 to allow a vertical spreading of the air passing through the air outlet 6.

Referring to FIG. 19, a plurality of UV sterilization modules 140, 141, and 142 may be arranged in the body 2 of the air conditioner. The plurality of UV sterilization modules 140, 141, and 142 may include a plurality of UV sterilization lamps 100 to generate UV rays. An inside of the air conditioner may be sterilized by the UV rays generated by the plurality of UV sterilization lamps 100. The heat exchanger 60 arranged in the air conditioner may also be sterilized. The plurality of UV sterilization modules 140, 141, and 142 may be installed in various directions in the air conditioner.

The heat exchanger 60 may exchange heat with the indoor air flowing in the air conditioner and a dew condensation phenomenon may occur due to a temperature difference between the refrigerant and the indoor air. As a relatively humid state is maintained, it is vulnerable to generation of bacteria and fungus. When the air conditioner operates in a state in which bacteria and fungus is generated, unhygienic air may be discharged in the indoor space, thus exerting a bad effect on a user's health.

The UV sterilization lamp 100 may be arranged in the air conditioner in a horizontal direction. The UV sterilization lamp 100 may be provided in a straight pipe shape elongated in a horizontal direction. For example, the UV sterilization lamp 100 may have a length (L1, see FIG. 1) of at least about 60 cm to about 70 cm. This length is a length based on a width of a general air conditioner. However, embodiments are not limited thereto.

Further, the power consumption for operating the plurality of UV sterilization lamps 100 may be at least about 30 W to about 60 W. This is because the UV sterilization lamp 100 generates more heat as the power consumption increases. When the heat generated by the UV sterilization lamp 100 increases, a cooling performance of the air conditioner may be reduced. Further, as the power consumption of the general air conditioner is usually high, it is preferable that the power consumption for operating the plurality of UV sterilization lamps 100 is low.

Therefore, in the this embodiment, it is assumed that the length of the UV sterilization lamp 100 is about 60 cm to about 70 cm, and the power consumption of the plurality of UV sterilization lamps 100, that is, the UV sterilization modules 140, 141, and 142 is about 30 W to about 60 W. The length and the power consumption of the UV sterilization lamp 100 are merely an example, and may be variously changed.

For example, one length (e.g., about 65 cm) of the lengths and the total power consumption (e.g., about 60 W) may be selected. The spacing and number of the UV sterilization lamps may be determined in consideration of the selected length and power consumption. The spacing between the UV sterilization lamps 100 may be about 1 cm to about 8 cm. However, embodiments are not limited thereto.

According to this embodiment, the UV sterilization modules 140, 141, and 142 may sterilize the inside of the air conditioner and the heat exchanger 60, and the sterilized indoor air may be discharged, thereby providing a pleasant indoor space. The UV sterilization modules 140, 141, and 142 may be respectively disposed or provided in the chassis 10, the front panel 28, and the filter frame 90. Further, the UV sterilization modules 140, 141, and 142 may also be installed in the front plate 20 as well as the front panel 28. However, embodiments are not limited thereto. In this embodiment, it is assumed that the UV sterilization modules 140, 141, and 142 are disposed or provided in the chassis 10, the front panel 28, and the filter frame 90.

More specifically, the UV sterilization modules 140, 141, and 142 may be respectively disposed or provided in the chassis 10, the front panel 28, and the filter frame 90. Even more specifically, the module body (121 in FIG. 10 or 131 in FIG. 13) of the UV sterilization module may be fixed to the chassis 10, the front panel 28, and the filter frame 90.

That is, the UV sterilization modules 140, 141, and 142 may be provided as a sterilizing apparatus in the air conditioner as a module itself. Alternatively, when the fixing portion (122 in FIG. 12) to which the plurality of UV sterilization lamps 100 may be directly fixed is provided in the air conditioner, the plurality of UV sterilization lamps 100 may also be directly mounted. However, embodiments are not limited thereto.

The plurality of UV sterilization modules 140, 141, and 142 may be arranged to be spaced from each other in a first zone Z-1, a second zone Z-2, and a third zone Z-3 in the air conditioner. The first zone Z-1 may be defined as a space between the filter frame 90 and the front panel 28. The second zone Z-2 may be defined as a space between the heat exchanger 60 and the fan 54 and the chassis 10. The third zone Z-3 may be defined as a space between the heat exchanger 60 and the fan 54 and the filter frame 90.

The plurality of UV sterilization modules 140, 141, and 142 may be arranged in one or more of the first zone Z-1, the second zone Z-2, and the third zone Z-3 in the air conditioner. For example, the plurality of UV sterilization modules 140, 141, and 142 may include a first UV sterilization module 140 disposed or provided in the first zone Z-1, a second UV sterilization module 141 disposed or provided in the second zone Z-2, and a third UV sterilization module 142 disposed or provided in the third zone Z-3.

The first UV sterilization module 140 and the second UV sterilization module 141 may be arranged adjacent to the chassis 10 and the front panel 28 in the air conditioner. That is, the sterilization may be performed in only one side direction due to the chassis 10 and the front panel 28. In this case, it is desirable to use the UV sterilization module 120 of FIG. 10.

The third UV sterilization module 142 may be arranged in a space between the heat exchanger 60 and the fan 54 and the filter frame 90. That is, the third UV sterilization module 142 may face the indoor air introduced via the air inlet 4 and moved toward the heat exchanger 60. In this case, it is desirable to use the UV sterilization module 130 of FIG. 13.

The plurality of UV sterilization modules 140, 141, and 142 may be arranged adjacent to the air outlet 6, except for the first, second, and third zones. However, embodiments are not limited thereto.

That is, the UV rays generated by the plurality of UV sterilization modules 140, 141, and 142 may simultaneously sterilize the inside of the air conditioner and the heat exchanger 60 in various directions. Therefore, bacteria and fungus generated in the heat exchanger 60 and the inside of the air conditioner may be intensively sterilized. The arrangement of the UV sterilization modules 140, 141, and 142 is merely an example, and embodiments are not limited thereto.

Referring to FIG. 17, when the air conditioner is operated, the fan 54 may be rotated. The rotation of the fan 54 may allow outside air P1 to be suctioned via the air inlet 4 of the air conditioner and then to have a heat exchange with the heat exchanger 60. The outside air P1 heat-exchanged with the heat exchanger 60 may be discharged via the air outlet 6 of the air conditioner.

When the air conditioner is operated, the plurality of UV sterilization modules 140, 141, and 142 disposed or provided in the internal space of the air conditioner may be operated. Alternatively, when operation of the air conditioner is stopped, operations of the plurality of UV sterilization modules 140, 141, and 142 may be stopped.

More specifically, power may be supplied to the plurality of UV sterilization modules 140, 141, and 142 disposed or provided in the internal space of the air conditioner. The plurality of UV sterilization modules 140, 141, and 142 may be respectively arranged in the first zone Z-1, the second zone Z-2, and the third zone Z-3.

When the power is supplied, the plurality of UV sterilization modules 140, 141, and 142 may generate UV rays. As the generated UV rays have the wavelength of UV-C suitable for sterilization, the internal space of the air conditioner may be efficiently sterilized.

That is, while the outside air P1 introduced via the air inlet 4 flows into the heat exchanger 60, the outside air P1 may be sterilized by the plurality of UV sterilization modules 140, 141, and 142 respectively arranged in the first zone Z-1, the second zone Z-2, and the third zone Z-3. The outside air P2 sterilized by the plurality of UV sterilization modules 140, 141, and 142 may be discharged via the air outlet 6 by the fan 54. That is, the outside air P2 sterilized by the plurality of UV sterilization lamps 100 may be discharged via the air outlet 6.

Additionally, even after the operation of the air conditioner is stopped, the heat exchanger 60 and the inside of the air conditioner may be sterilized by the plurality of UV sterilization modules 140, 141, and 142. Therefore, the quality of the air discharged from the air conditioner may be improved. As bacteria and fungus which may be propagated through the air is removed, it is possible to prevent infectious diseases propagated through the air.

In this embodiment, the wall-mounted air conditioner has been described by way of example, but the UV sterilization lamp 100 and the UV sterilization module 110 may be used in various fields, such as a stand-type air conditioner and an air cleaner, for example. However, embodiments are not limited thereto.

Figure 21A:
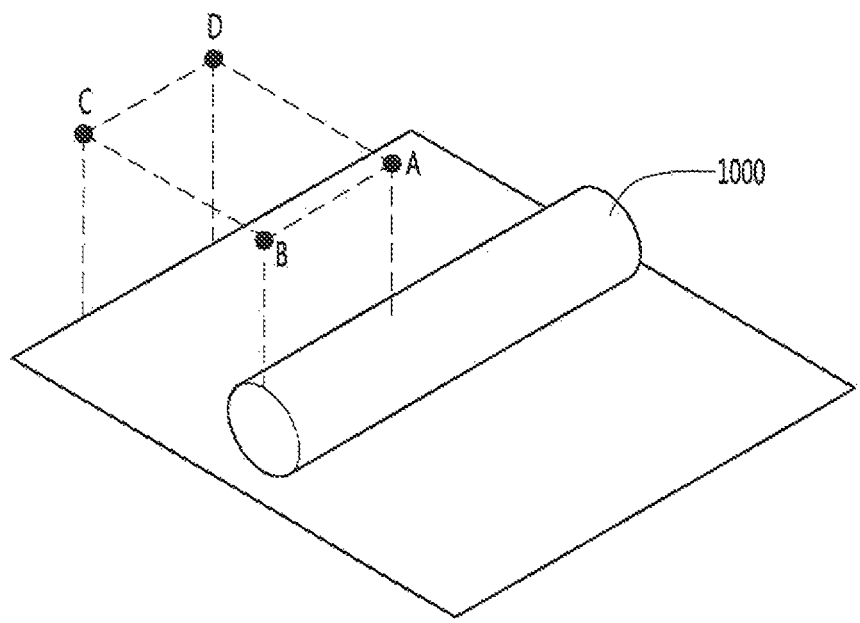
FIGS. 21A-21B are diagrams for describing power energies measured in a given region when a conventional UV lamp is employed.
Figure 21B:
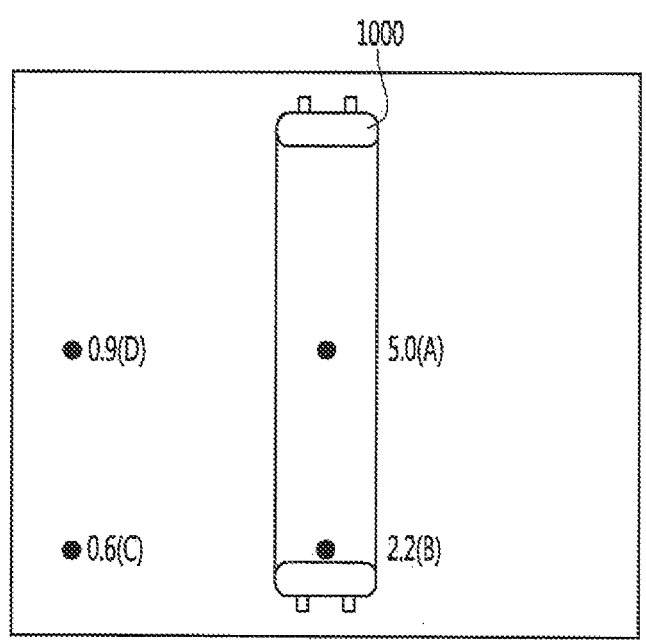
Figure 22A:
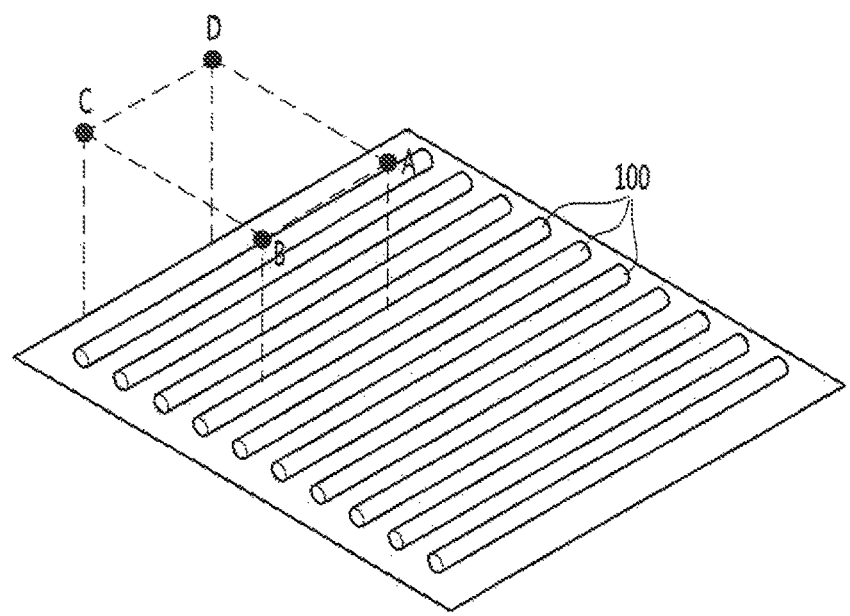
FIGS. 22A-22B are diagram for describing power energies measured in a given region when the UV sterilization lamp in accordance with embodiments is employed.
Figure 22B:
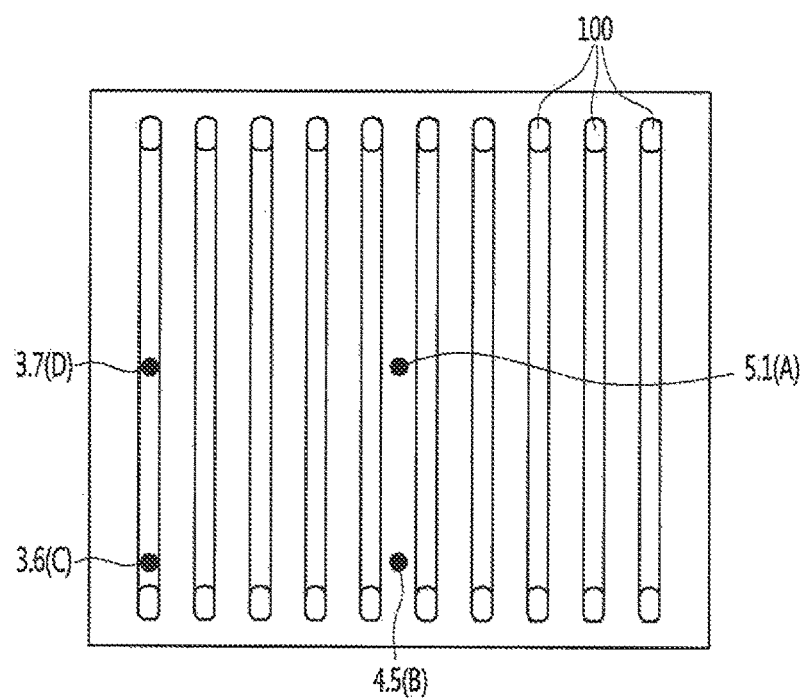

FIGS. 21A-21B are diagrams for describing power energies measured in a given region when a conventional UV lamp is employed. FIGS. 22A-22B are diagrams for describing power energies measured in a given region when the UV sterilization lamp in accordance embodiments is employed.

In FIGS. 21A-21B, a single conventional UV lamp 1000 is used to conduct UV sterilization, while in FIGS. 22A-22B, in one embodiment, a parallel connection of ten UV sterilization lamps 100 is used to conduct UV sterilization. As shown in FIGS. 21A-21B, when the single conventional UV lamp 1000 works, power energy measured in an A region amounts to about 5 m W/cm$^2$; power energy measured in a B region amounts to about 2.2 mW/cm$^2$; power energy measured in a C region amounts to about 0.6 mW/cm$^2$; and power energy measured in a D region amounts to about 0.9 mW/cm$^2$. In this case, the total power consumption of the conventional UV lamp 1000 is about 15 W and the diameter thereof is about 28 mm.

As shown in FIGS. 22A-22B, when the ten UV lamps 100 arranged in parallel according to an embodiment work, power energy measured in an A region amounts to about 5.1 W/cm$^2$; power energy measured in a B region amounts to about 4.5 mW/cm$^2$; power energy measured in a C region amounts to about 3.6 mW/cm$^2$; and power energy measured in a D region amounts to about 3.7 mW/cm$^2$. In this case, the total power consumption of the UV sterilization lamps 100 is about 15 W, the diameter thereof is about 3 mm, and the spacing between different UV sterilization lamps 100 is about 1 cm.

That is, in one embodiment, when a plurality of the UV sterilization lamps 100 with small diameters respectively works concurrently, a high power density may be achieved due to a small spacing between the lamps, and thus, an overlapping effect. In contrast, lower power density may be achieved due to a larger spacing between the lamps, and thus, a reduced overlapping effect.

When comparing power consumption between the case in which one conventional UV lamp 1000 works with the case in which the ten UV sterilization lamps 100 according to embodiments work, lower power is consumed in the case in which the ten UV sterilization lamps 100 according to embodiments work at the same time. Thus, the case of using the plurality of UV sterilization lamps 100 according embodiments is more efficient than the case of using the conventional UV lamp in consideration of power consumption, space efficiency, and UV sterilization effect.

Embodiments disclosed herein provide a UV sterilization module which is capable of uniformly sterilizing a certain area. Embodiments disclosed herein further provide a desirable spacing between UV sterilization lamps which are capable of uniformly sterilizing a certain area. Embodiments disclosed herein provide a UV sterilization module which has increased space efficiency so as to be usable in various spaces.

Embodiments disclosed herein also provide a UV sterilization module which has low power consumption. Embodiments disclosed herein additionally provide an air conditioner including the UV sterilization module.

A UV sterilization module in accordance with embodiments may include a porous frame; a plurality of UV lamps disposed or provided on the porous frame; a power supply connected to the plurality of UV lamps to supply power; and a plurality of fixing portions configured to support the plurality of UV lamps and fixed to the porous frame. The plurality of fixing portions may be spaced at a constant spacing such that the plurality of UV lamps may be spaced from each other. The constant spacing may be a shortest distance of about 8 cm or less to connect outer peripheral surfaces of the plurality of UV lamps adjacent to each other. The plurality of UV lamps may have a same outer diameter.

Further, the plurality of UV lamps may be arranged in parallel to a direction toward a width of the porous frame. Furthermore, the plurality of UV lamps may be arranged to be spaced from each other toward a length of the porous frame at a constant spacing. As the constant spacing increases, a number of UV lamps may be reduced. Also, the plurality of UV lamps may be formed to be smaller than the width of the porous frame.

An air conditioner according to embodiments may include a main body having an inlet and an outlet to allow an air to flow in and out; a heat exchanger disposed or provided in an internal space of the main body and configured to allow heat exchange with the air; a blower fan configured to forcibly circulate the air heat-exchanged by the heat exchanger; and at least one UV sterilization module disposed or provided in the internal space of the main body to sterilize the air introduced into the internal space of the main body and an inside of the main body. As a size of the UV sterilization module is reduced, the UV sterilization lamp may be arranged in various spaces.

Further, a uniform area may be sterilized through the small-sized UV sterilization module, thereby increasing sterilization efficiency. Furthermore, it is possible to provide the optimized spacing between small-sized UV sterilization lamps.

Additionally, the power consumption may be reduced, thereby obtaining expense profit. Also, as a small amount of Hg is included, it is eco-friendly.

Moreover, it is possible to obtain strong sterilizing power due to the generated UV-C wavelength, and as an external electrode type is used, parallel connection and a long lifespan of the lamp may be ensured. The UV sterilization module may be modularized, and thus, may be used in various fields.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A ultraviolet (UV) sterilization module, comprising:
   a porous frame, a portion of which is a mesh that allows a fluid to pass therethrough;
   a plurality of UV lamps provided on the mesh of the porous frame and Including an external electrode on an outer surface thereof;
   a power supply connected to the plurality of UV lamps to supply power to the plurality of UV lamps; and
   a plurality of fixing portions configured to support the plurality of UV lamps and fixed to the porous frame, wherein the plurality of fixing portions is arranged to be spaced from each other such that the plurality of UV lamps is arranged with a constant spacing, and wherein the constant spacing is a shortest distance of about 8 cm or less to connect outer peripheral surfaces of the plurality of UV lamps adjacent to each other.

2. The UV sterilization module of claim 1, wherein the constant spacing is at least about 1 cm or more, wherein an outer diameter of each of the plurality of UV lamps is smaller than the constant spacing.

3. The UV sterilization module of claim 2, wherein each of the plurality of UV lamps has an inner diameter of at least about 0.7 mm or more and an outer diameter of about 1 mm to about 7 mm.

4. The UV sterilization module of claim 1, wherein the porous frame has a constant width and a length longer than the width, wherein the plurality of UV lamps is arranged in parallel to a widthwise direction and is spaced about from each other in a lengthwise direction at the constant spacing.

5. The UV sterilization module of claim 4, wherein the plurality of UV lamps is smaller than the width of the porous frame.

6. The UV sterilization module of claim 1, wherein the plurality of fixing portions is a plurality of conductive fixing portions configured to receive power from the power supply and supply the power to the plurality of UV lamps, and further comprising at least one electrode rail provided in the porous frame, wherein the plurality of conductive fixing portions is provided on the at least one electrode rail.

7. A ultraviolet (UV) sterilization module, comprising:
   a first UV lamp having a first outer diameter and a first length in a lengthwise direction of the UV sterilization module;

a second UV lamp having a second outer diameter and a second length in the lengthwise direction of the UV sterilization module;
a pair of first fixing devices configured to surround the first outer diameter of the first UV lamp;
a pair of second fixing devices configured to surround the second outer diameter of the second UV lamp;
a module body configured to support the pair of first fixing portions and the pair of second fixing portions and have at least flexibility or elasticity; and
a power supply configured to connect the first UV lamp and the second UV lamp in parallel to supply power thereto, wherein a passage having a width of about 1 cm to about 8 cm to allow at least a fluid to pass therethrough is formed between the first outer diameter of the first UV lamp and the second outer diameter of the second UV lamp.

8. The UV sterilization module of claim 7, wherein the first outer diameter of the first UV lamp is equal to the second diameter of the second UV lamp, and the first outer diameter of the first UV lamp and the second outer diameter of the second UV lamp are about 1 mm to about 7 mm.

9. The UV sterilization module of claim 7, wherein a width of the passage is larger than the first outer diameter of the first UV lamp and the second outer diameter of the second UV lamp.

10. An air conditioner, comprising:
a main body having an air inlet and an air outlet;
a heat exchanger provided in the main body and configured to allow heat exchange with air introduced via the air inlet;
a blower fan provided in the main body and configured to blow the air heat-exchanged with the heat exchanger toward the air outlet; and
at least one UV sterilization module configured to sterilize the air introduced via the air inlet and an inside of the main body with UV rays, wherein the UV sterilizer module includes:
at least two UV lamps configured to generate UV rays and arranged to be spaced from each other;
a plurality of fixing portions respectively mounted on the at least two UV lamps;
a porous body configured to support the plurality of fixing portions and provided in the main body, a portion of the porous body being a mesh; and
a power supply connected to the at least two UV lamps to supply power to the at least two UV lamps,
wherein a length of a tangent line that connects outer peripheral surfaces of the at least two UV lamps is about 8 cm or less.

11. The air conditioner of claim 10, wherein the at least one UV sterilization module surrounds at least the heat exchanger in the main body.

12. The air conditioner of claim 10, wherein each of the at least two UV lamps has an outer diameter of about 1 mm to about 7 mm.

13. The air conditioner of claim 10, wherein the at least two UV lamps are arranged in a lengthwise direction of the main body.

14. A ultraviolet (UV) sterilization module, comprising:
a porous frame, a portion of which is a mesh that allows a fluid to pass therethrough;
a plurality of UV lamps provided on the mesh of the porous frame and including an external electrode on an outer surface thereof;
a power supply connected to the plurality of UV lamps to supply power to the plurality of UV lamps; and
a plurality of supports configured to support the plurality of UV lamps and fixed to the porous frame, wherein the plurality of supports is each shaped to surround a portion of an outer diameter of one of the plurality of UV lamps, respectively, wherein the plurality of supports is arranged to be spaced from each other such that the plurality of UV lamps is arranged with a constant spacing, and wherein the constant spacing is a shortest distance of about 8 cm or less to connect outer peripheral surfaces of the plurality of UV lamps adjacent to each other.

15. The UV sterilization module of claim 14, wherein the constant spacing is at least about 1 cm or more, wherein each of the plurality of UV lamps has an inner diameter of at least about 0.7 mm or more and the outer diameter is about 1 mm to about 7 mm.

16. The UV sterilization module of claim 15, wherein the outer diameter of each of the plurality of UV lamps is smaller than the constant spacing, wherein the plurality of UV lamps has the same outer diameter.

17. The UV sterilization module of claim 14, wherein the plurality of supports is a plurality of conductive supports configured to receive power from the power supply and supply the power to the plurality of UV lamps, wherein the UV sterilization module further including at least one electrode rail provided in the porous frame, and wherein the plurality of conductive supports is provided on the at least one electrode rail.

* * * * *